(12) United States Patent
Taylor et al.

(10) Patent No.: US 6,984,987 B2
(45) Date of Patent: Jan. 10, 2006

(54) ELECTRO-KINETIC AIR TRANSPORTER AND CONDITIONER DEVICES WITH ENHANCED ARCHING DETECTION AND SUPPRESSION FEATURES

(75) Inventors: Charles E. Taylor, Punta Gorda, FL (US); Shek Fai Lau, Foster City, CA (US); Andrew J. Parker, Novato, CA (US); Greg S. Snyder, Novato, CA (US); Edward C. McKinney, Jr., Novato, CA (US)

(73) Assignee: Sharper Image Corporation, San Francisco, CA (US)

( * ) Notice: Subject to any disclaimer, the term of this patent is extended or adjusted under 35 U.S.C. 154(b) by 125 days.

(21) Appl. No.: 10/625,401

(22) Filed: Jul. 23, 2003

(65) Prior Publication Data

US 2004/0251909 A1 Dec. 16, 2004

Related U.S. Application Data

(60) Provisional application No. 60/477,980, filed on Jun. 12, 2003.

(51) Int. Cl.
   *H02H 3/08* (2006.01)
   *G01R 31/14* (2006.01)
   *G01R 31/08* (2006.01)

(52) U.S. Cl. ................. 324/509; 324/522; 361/93.1

(58) Field of Classification Search ............... 324/509, 324/522, 536, 459, 464, 466; 361/94, 93.1, 361/89; 422/186.04, 486.21, 186.28; 96/6, 96/7; 95/20–24
   See application file for complete search history.

(56) References Cited

U.S. PATENT DOCUMENTS

| | | |
|---|---|---|
| 653,421 A | 7/1900 | Lorey |
| 995,958 A | 6/1911 | Goldberg |
| 1,791,338 A | 2/1931 | Wintermute |
| 1,869,335 A | 7/1932 | Day |
| 2,327,588 A | 8/1943 | Bennett |
| 2,359,057 A | 9/1944 | Skinner |
| 2,509,548 A | 5/1950 | White |
| 2,949,550 A | 8/1960 | Brown |
| 3,018,394 A | 1/1962 | Brown |

(Continued)

FOREIGN PATENT DOCUMENTS

CN 2111112 U 7/1972

(Continued)

OTHER PUBLICATIONS

U.S. Appl. No. 09/197,131, filed Nov. 20, 1998, Taylor et al.

(Continued)

*Primary Examiner*—Anjan Deb
*Assistant Examiner*—John Teresinski
(74) *Attorney, Agent, or Firm*—Bell, Boyd & Lloyd

(57) ABSTRACT

Systems and methods are provided for monitoring and suppressing arcing between a first electrode and a second electrode of an electro-kinetic system. A current (or voltage) associated with the electro-kinetic system is monitored in order to adjust a first count and a second count. Each time a monitored value reaches a threshold, the first count is incremented. Each time the first count reaches a first count threshold, the electro-kinetic system is temporarily shut down for a predetermined period, the second count is incremented, and the first count is re-initialized. The electro-kinetic system restarts after the predetermined period. When the second count reaches a second count threshold, the electro-kinetic system is shut-down until a reset condition is satisfied.

41 Claims, 13 Drawing Sheets

U.S. PATENT DOCUMENTS

| | | |
|---|---|---|
| 3,026,964 A | 3/1962 | Penney |
| 3,374,941 A | 3/1968 | Okress |
| 3,518,462 A | 6/1970 | Brown |
| 3,540,191 A | 11/1970 | Herman |
| 3,581,470 A | 6/1971 | Aitkenhead et al. |
| 3,638,058 A | 1/1972 | Fritzius |
| 3,744,216 A | 7/1973 | Halloran |
| 3,981,695 A | 9/1976 | Fuchs |
| 3,984,215 A | 10/1976 | Zucker |
| 4,052,177 A | 10/1977 | Kide |
| 4,092,134 A | 5/1978 | Kikuchi |
| 4,102,654 A | 7/1978 | Pellin |
| 4,138,233 A | 2/1979 | Masuda |
| 4,209,306 A | 6/1980 | Feldman et al. |
| 4,227,894 A | 10/1980 | Proynoff |
| 4,231,766 A | 11/1980 | Spurgin |
| 4,232,355 A | 11/1980 | Finger et al. |
| 4,244,710 A | 1/1981 | Burger |
| 4,244,712 A | 1/1981 | Tongret |
| 4,253,852 A | 3/1981 | Adams |
| 4,259,452 A | 3/1981 | Yukuta et al. |
| 4,266,948 A | 5/1981 | Teague et al. |
| 4,282,014 A | 8/1981 | Winkler et al. |
| 4,284,420 A | 8/1981 | Borysiak |
| 4,318,718 A | 3/1982 | Utsumi et al. |
| 4,342,571 A | 8/1982 | Hayashi |
| 4,357,150 A | 11/1982 | Masuda et al. |
| 4,386,395 A | 5/1983 | Francis, Jr. |
| 4,413,225 A | 11/1983 | Donig et al. |
| 4,445,911 A | 5/1984 | Lind |
| 4,477,263 A | 10/1984 | Shaver et al. |
| 4,496,375 A | 1/1985 | Le Vantine |
| 4,502,002 A | 2/1985 | Ando |
| 4,509,958 A | 4/1985 | Masuda et al. |
| 4,516,991 A | 5/1985 | Kawashima |
| 4,536,698 A | 8/1985 | Shevalenko et al. |
| 4,587,475 A | 5/1986 | Finney, Jr. et al. |
| 4,600,411 A | 7/1986 | Santamaria |
| 4,601,733 A | 7/1986 | Ordines et al. |
| 4,626,261 A | 12/1986 | Jorgensen |
| 4,643,745 A | 2/1987 | Sakakibara et al. |
| 4,659,342 A | 4/1987 | Lind |
| 4,674,003 A | 6/1987 | Zylka |
| 4,686,370 A | 8/1987 | Blach |
| 4,689,056 A | 8/1987 | Noguchi et al. |
| 4,694,376 A | 9/1987 | Gesslauer |
| 4,713,093 A | 12/1987 | Hansson |
| 4,713,724 A | 12/1987 | Voelkel |
| 4,726,812 A | 2/1988 | Hirth |
| 4,726,814 A | 2/1988 | Weitman |
| 4,772,297 A | 9/1988 | Anzai |
| 4,779,182 A | 10/1988 | Mickal et al. |
| 4,781,736 A | 11/1988 | Cheney et al. |
| 4,786,844 A | 11/1988 | Farrell et al. |
| 4,789,801 A | 12/1988 | Lee |
| 4,808,200 A | 2/1989 | Dallhammer et al. |
| 4,811,159 A | 3/1989 | Foster, Jr. |
| 4,940,470 A | 7/1990 | Jaisinghani et al. |
| 4,941,068 A | 7/1990 | Hofmann |
| 4,955,991 A | 9/1990 | Torok et al. |
| 4,967,119 A | 10/1990 | Torok et al. |
| 4,976,752 A | 12/1990 | Torok et al. |
| D315,598 S | 3/1991 | Yamamoto et al. |
| 5,006,761 A | 4/1991 | Torok et al. |
| 5,009,764 A * | 4/1991 | Siefkes et al. ......... 204/298.08 |
| 5,010,869 A | 4/1991 | Lee |
| 5,012,093 A | 4/1991 | Shimizu |
| 5,012,159 A | 4/1991 | Torok et al. |
| 5,024,685 A | 6/1991 | Torok et al. |
| 5,053,912 A | 10/1991 | Loreth et al. |
| 5,077,500 A | 12/1991 | Torok et al. |
| RE33,927 E | 5/1992 | Fuzimura |
| 5,141,529 A | 8/1992 | Oakley et al. |
| D329,284 S | 9/1992 | Patton |
| D332,655 S | 1/1993 | Lytle et al. |
| 5,180,404 A | 1/1993 | Loreth et al. |
| 5,183,480 A | 2/1993 | Raterman et al. |
| 5,196,171 A | 3/1993 | Peltier |
| 5,215,558 A | 6/1993 | Moon |
| 5,217,504 A | 6/1993 | Johansson |
| 5,248,324 A | 9/1993 | Hara |
| 5,266,004 A | 11/1993 | Tsumurai et al. |
| 5,290,343 A | 3/1994 | Morita et al. |
| 5,296,019 A | 3/1994 | Oakley et al. |
| 5,302,190 A | 4/1994 | Williams |
| 5,315,838 A | 5/1994 | Thompson |
| 5,316,741 A | 5/1994 | Sewell et al. |
| 5,378,978 A | 1/1995 | Gallo et al. |
| 5,435,817 A | 7/1995 | Davis et al. |
| 5,437,713 A | 8/1995 | Chang |
| 5,484,472 A | 1/1996 | Weinberg |
| 5,532,798 A | 7/1996 | Nakagami et al. |
| 5,535,089 A | 7/1996 | Ford et al. |
| D375,546 S | 11/1996 | Lee |
| 5,578,112 A | 11/1996 | Krause |
| D377,523 S | 1/1997 | Marvin et al. |
| 5,601,636 A | 2/1997 | Glucksman |
| 5,641,342 A | 6/1997 | Smith et al. |
| 5,656,063 A | 8/1997 | Hsu |
| 5,667,564 A | 9/1997 | Weinberg |
| 5,669,963 A | 9/1997 | Horton et al. |
| 5,698,164 A | 12/1997 | Kishioka et al. |
| 5,702,507 A | 12/1997 | Wang |
| D389,567 S | 1/1998 | Gudefin |
| 5,779,769 A | 7/1998 | Jiang |
| 5,814,135 A | 9/1998 | Weinberg |
| 5,879,435 A | 3/1999 | Satyapal et al. |
| 5,893,977 A | 4/1999 | Pucci |
| 5,911,957 A | 6/1999 | Khatchatrian et al. |
| 5,972,076 A | 10/1999 | Nichols et al. |
| 5,975,090 A | 11/1999 | Taylor et al. |
| 5,980,614 A | 11/1999 | Loreth et al. |
| 5,993,521 A | 11/1999 | Loreth et al. |
| 5,997,619 A | 12/1999 | Knuth et al. |
| 6,019,815 A | 2/2000 | Satyapal et al. |
| 6,042,637 A | 3/2000 | Weinberg |
| 6,063,168 A | 5/2000 | Nichols et al. |
| 6,086,657 A | 7/2000 | Freije |
| 6,115,230 A * | 9/2000 | Voigts et al. ............... 361/230 |
| 6,117,216 A | 9/2000 | Loreth |
| 6,118,645 A | 9/2000 | Partridge |
| 6,126,722 A | 10/2000 | Mitchell et al. |
| 6,126,727 A | 10/2000 | Lo |
| 6,149,717 A | 11/2000 | Satyapal et al. |
| 6,149,815 A | 11/2000 | Sauter |
| 6,152,146 A | 11/2000 | Taylor et al. |
| 6,163,098 A | 12/2000 | Taylor et al. |
| 6,176,977 B1 | 1/2001 | Taylor et al. |
| 6,182,461 B1 | 2/2001 | Washburn et al. |
| 6,182,671 B1 | 2/2001 | Taylor et al. |
| 6,193,852 B1 | 2/2001 | Caracciolo et al. |
| 6,203,600 B1 | 3/2001 | Loreth |
| 6,212,883 B1 | 4/2001 | Kang |
| 6,228,149 B1 | 5/2001 | Alenichev et al. |
| 6,252,012 B1 | 6/2001 | Egitto et al. |
| 6,270,733 B1 | 8/2001 | Rodden |
| 6,277,248 B1 | 8/2001 | Ishioka et al. |
| 6,282,106 B2 | 8/2001 | Grass |
| D449,097 S | 10/2001 | Smith et al. |
| D449,679 S | 10/2001 | Smith et al. |
| 6,302,944 B1 | 10/2001 | Hoenig |
| 6,309,514 B1 | 10/2001 | Conrad et al. |
| 6,312,507 B1 | 11/2001 | Taylor et al. |
| 6,315,821 B1 | 11/2001 | Pillion et al. |

| | | | |
|---|---|---|---|
| 6,328,791 | B1 | 12/2001 | Pillion et al. |
| 6,348,103 | B1 | 2/2002 | Ahlborn et al. |
| 6,350,417 | B1 | 2/2002 | Lau et al. |
| 6,362,604 | B1 | 3/2002 | Cravey |
| 6,368,391 | B1 * | 4/2002 | O'Hara et al. ............... 96/18 |
| 6,372,097 | B1 | 4/2002 | Chen |
| 6,373,723 | B1 | 4/2002 | Wallgren et al. |
| 6,379,427 | B1 | 4/2002 | Siess |
| 6,391,259 | B1 | 5/2002 | Malkin et al. |
| 6,398,852 | B1 | 6/2002 | Loreth |
| 6,447,021 | B1 * | 9/2002 | Haynes ................... 285/302 |
| 6,447,587 | B1 | 9/2002 | Pillion et al. |
| 6,464,754 | B1 | 10/2002 | Ford |
| 6,471,753 | B1 | 10/2002 | Ahn et al. |
| 6,494,940 | B1 | 12/2002 | Hak |
| 6,504,308 | B1 | 1/2003 | Krichtafovitch et al. |
| 6,508,982 | B1 | 1/2003 | Shoji |
| 6,603,268 | B2 | 8/2003 | Lee |
| 6,613,277 | B1 | 9/2003 | Monagan |
| 6,635,105 | B2 | 10/2003 | Ahlborn et al. |
| 2002/0069760 | A1 | 6/2002 | Pruette et al. |
| 2002/0144601 | A1 | 10/2002 | Palestro et al. |
| 2002/0152890 | A1 | 10/2002 | Leiser |
| 2002/0170435 | A1 | 11/2002 | Joannou |
| 2002/0190658 | A1 | 12/2002 | Lee |
| 2003/0005824 | A1 | 1/2003 | Katou et al. |
| 2004/0033176 | A1 | 2/2004 | Lee et al. |
| 2004/0052700 | A1 | 3/2004 | Kotlyar et al. |
| 2004/0065202 | A1 | 4/2004 | Gatchell et al. |
| 2004/0136863 | A1 | 7/2004 | Yates et al. |
| 2004/0166037 | A1 | 8/2004 | Youdell et al. |
| 2004/0226447 | A1 | 11/2004 | Lau et al. |
| 2004/0234431 | A1 | 11/2004 | Taylor et al. |
| 2004/0237787 | A1 | 12/2004 | Reeves et al. |
| 2004/0251124 | A1 | 12/2004 | Lau |
| 2004/0251909 | A1 | 12/2004 | Taylor et al. |
| 2005/0000793 | A1 | 1/2005 | Taylor et al. |

FOREIGN PATENT DOCUMENTS

| | | |
|---|---|---|
| CN | 87210843 U | 7/1988 |
| CN | 2138764 Y | 6/1993 |
| CN | 2153231 Y | 12/1993 |
| CN | 2174002 Y | 8/1994 |
| DE | 2206057 | 8/1973 |
| EP | 0433152 A1 | 12/1990 |
| EP | 0332624 B1 | 1/1992 |
| FR | 2690509 | 10/1993 |
| GB | 643363 | 9/1950 |
| JP | S51-90077 | 8/1976 |
| JP | S62-20653 | 2/1987 |
| JP | 10137007 | 5/1998 |
| JP | 10216561 | 8/1998 |
| JP | 11104223 | 4/1999 |
| JP | 2000236914 | 9/2000 |
| WO | WO92/05875 A1 | 4/1992 |
| WO | WO96/04703 A1 | 2/1996 |
| WO | WO99/07474 A1 | 2/1999 |
| WO | WO00/10713 A1 | 3/2000 |
| WO | WO01/47803 A1 | 7/2001 |
| WO | WO 01/47803 A1 | 7/2001 |
| WO | WO 01/48781 A1 | 7/2001 |
| WO | WO01/64349 A1 | 9/2001 |
| WO | WO01/85348 A2 | 11/2001 |
| WO | WO02/20162 A2 | 3/2002 |
| WO | WO02/20163 A2 | 3/2002 |
| WO | WO02/30574 A1 | 4/2002 |
| WO | WO02/32578 A1 | 4/2002 |
| WO | WO02/42003 A1 | 5/2002 |
| WO | WO02/066167 A1 | 8/2002 |
| WO | WO03/009944 A1 | 2/2003 |
| WO | WO03/013620 A1 | 2/2003 |
| WO | WO03/013734 AA | 2/2003 |

OTHER PUBLICATIONS

U.S. Appl. No. 09/669,253, filed Sep. 25, 2000, Taylor et al.
U.S. Appl. No. 09/669,268, filed Sep. 25, 2000, Taylor et al.
U.S. Appl. No. 09/730,499, filed Dec. 5, 2000, Taylor et al.
U.S. Appl. No. 09/742,814, filed Dec. 19, 2000, Taylor et al.
U.S. Appl. No. 09/774,198, filed Jan, 29, 2001, Taylor.
U.S. Appl. No. 60/306,479, Taylor, filed Jul. 18, 2001.
U.S. Appl. No. 09/924,600, filed Aug. 8, 2001, Taylor et al.
U.S. Appl. No. 09/924,624, filed Aug. 8, 2001, Taylor et al.
U.S. Appl. No. 60/340,288, Taylor, filed Dec. 13, 2001.
U.S. Appl. No. 60/340,462, Taylor, filed Dec. 13, 2001.
U.S. Appl. No. 60/340,702, Taylor et al., filed Dec. 13, 2001.
U.S. Appl. No. 60/341,090, Taylor, filed Dec. 13, 2001.
U.S. Appl. No. 60/341,176, Taylor, filed Dec. 13, 2001.
U.S. Appl. No. 60/341,179, Taylor et al., filed Dec. 13, 2001.
U.S. Appl. No. 60/341,320, Taylor, filed Dec. 13, 2001.
U.S. Appl. No. 60/341,377, Taylor et al., filed Dec. 13, 2001.
U.S. Appl. No. 60/341,433, Taylor, filed Dec. 13, 2001.
U.S. Appl. No. 60/341,518, Taylor, filed Dec. 13, 2001.
U.s. Appl. No. 60/341,592, Taylor, filed Dec. 13, 2001.
U.S. Appl. No. 10/023,197, filed Dec. 13, 2001, Taylor et al.
U.S. Appl. No. 10/023,460, filed Dec. 13, 2001, Taylor et al.
U.S. Appl. No. 10/074,082, filed Feb. 12, 2002, Taylor et al.
U.S. Appl. No. 10/074,096, filed Feb. 12, 2002, Taylor et al.
U.S. Appl. No. 10/074,103, filed Feb. 12, 2002, Sinaiko et al.
U.S. Appl. No. 10/074,207, filed Feb. 12, 2002, Taylor et al.
U.S. Appl. No. 10/074,208, filed Feb. 12, 2002, Taylor.
U.S. Appl. No. 10/074,209, filed Feb. 12, 2002, Taylor et al.
U.S. Appl. No. 10/074,339, filed Feb. 12, 2002, Taylor et al.
U.S. Appl. No. 10/074,347, filed Feb. 12, 2002, Taylor et al.
U.S. Appl. No. 10/074,379, filed Feb. 12, 2002, Taylor et al.
U.S. Appl. No. 10/074,549, filed Feb. 12, 2002, Sinaiko et al.
U.S. Appl. No. 10/074,827, filed Feb. 12, 2002, McKinney, Jr. et al.
U.S. Appl. No. 10/156,158, filed May 28, 2002, Taylor et al.
U.S. Appl. No. 60/391,070, Reeves, filed Jun. 6, 2002.
U.S. Appl. No. 10/188,668, filed Jul. 2, 2002, Taylor et al.
Electrical schematic and promotional material available from Zenion Industries, 7 pages, Aug. 1990.
Promotional material available from Zenion Industries for the Plasma-Pure 100/200/300, 2 pages, Aug. 1990.
Promotional material available from Zenion Industries for the Plasma-Tron, 2 pages, Aug. 1990.
LENTEK Silā™ Plug-In Air Purifier/Deodorizer product box copyrighted 1999, 13 pages.
U.S. Appl. No. 60/104,573, Krichtafovitch, filed Oct. 16, 1998.
Trion Console 250 Electronic Air Cleaner, Model Series 442857 and 445600, Manual for Installation•Operation•Maintenance, Trion Inc., 7 pp., believed to be at least one year prior to Nov. 5, 1998.
Trion 350 Air Purifier, Model 450111-010, http://www.feddersoutlet.com/trion350.html, 12 pp., believed to be at least one year prior to Nov. 5, 1998.
Trion 150 Air Purifier, Model 45000-002, http://www.feddersoutlet.com/trion150.html, 11 pp., believed to be at least one year prior to Nov. 5, 1998.
Trion 120 Air Purifier, Model 442501-025, http://www.feddersoutled.com/trion120.html, 16 pp., believed to be at least one year prior to Nov. 5, 1998.

Friedrich C-90A Electronic Air Cleaner, Service Information, Friedrich Air Conditioning Co., 12 pp., 1985.

LakeAir Excel and Maxum Portable Electronic Air Cleaners, Operating and Service Manual, LakeAir International, Inc., 11 pp., 1971.

Blueair AV 402 Air Purifier, http://www.air-purifiers-usa.biz/Blueair_AV402.htm, 4 pp., 1996.

Blueair AV 501 Air Purifier, http://www.air-purifiers-usa.biz/Blueair_AV501.htm, 15 pp., 1997.

* cited by examiner

ELECTRO-KINETIC AIR TRANSPORTER AND CONDITIONER DEVICES WITH ENHANCED ARCHING DETECTION AND SUPPRESSION FEATURES

PRIORITY CLAIM

This application claims priority under 35 U.S.C. 119(e) to U.S. Provisional Patent Application No. 60/477,980, filed Jun. 12, 2003, entitled "ELECTRO-KINETIC AIR TRANSPORTER AND CONDITIONER DEVICES WITH ENHANCED ARCING DETECTION AND SUPPRESSION FEATURES," which is incorporated herein by reference.

RELATED APPLICATION

This application is related to commonly assigned U.S. patent application Ser. No. 10/435,289, filed May 9, 2003, entitled "ELECTRO-KINETIC AIR TRANSPORTER AND CONDITIONER DEVICES WITH SPECIAL DETECTORS AND INDICATORS", which is incorporated herein by reference.

FIELD OF THE INVENTION

The present invention relates generally to devices that transport and/or condition air.

BACKGROUND OF THE INVENTION

FIG. 1 depicts a generic electro-kinetic device 10 to condition air. Device 10 includes a housing 20 that typically has at least one air input 30 and at least one air output 40. Within housing 20 there is disposed an electrode assembly or system 50 comprising a first electrode array 60 having at least one electrode 70 and comprising a second electrode array 80 having at least one electrode 90. System 10 further includes a high voltage generator 95 coupled between the first and second electrode arrays. As a result, ozone and ionized particles of air are generated within device 10, and there is an electro-kinetic flow of air in the direction from the first electrode array 60 towards the second electrode array 80. In FIG. 1, the large arrow denoted IN represents ambient air that can enter input port 30. The small "x"'s denote particulate matter that may be present in the incoming ambient air. The air movement is in the direction of the large arrows, and the output airflow, denoted OUT, exits device 10 via outlet 40. An advantage of electro-kinetic devices such as device 10 is that an airflow is created without using fans or other moving parts. Thus, device 10 in FIG. 1 can function somewhat as a fan to create an output airflow, but without requiring moving parts.

Preferably particulate matter "x" in the ambient air can be electrostatically attracted to the second electrode array 80, with the result that the outflow (OUT) of air from device 10 not only contains ozone and ionized air, but can be cleaner than the ambient air. In such devices, it can become necessary to occasionally clean the second electrode array electrodes 80 to remove particulate matter and other debris from the surface of electrodes 90. Accordingly, the outflow of air (OUT) is conditioned in that particulate matter is removed and the outflow includes appropriate amounts of ozone, and some ions.

An outflow of air containing ions and ozone may not, however, destroy or significantly reduce microorganisms such as germs, bacteria, fungi, viruses, and the like, collectively hereinafter "microorganisms." It is known in the art to destroy such microorganisms with, by way of example only, germicidal lamps. Such lamps can emit ultraviolet radiation having a wavelength of about 254 nm. For example, devices to condition air using mechanical fans, HEPA filters, and germicidal lamps are sold commercially by companies such as Austin Air, C.A.R.E. 2000, Amaircare, and others. Often these devices are somewhat cumbersome, and have the size and bulk of a small filing cabinet. Although such fan-powered devices can reduce or destroy microorganisms, the devices tend to be bulky, and are not necessarily silent in operation.

SUMMARY OF THE PRESENT INVENTION

Embodiments of the present invention relate to systems and methods for monitoring and suppressing arcing between a first electrode and a second electrode of an electro-kinetic system. A current (or voltage) associated with the arcing condition of the electro-kinetic system is monitored in order to adjust a first count and a second count. Each time a monitored value reaches a threshold, the first count is incremented. Each time the first count reaches a first count threshold (e.g., 30), the electro-kinetic system is temporarily shut down (or power is lowered) for a predetermined period (e.g., 80 seconds), the second count is incremented, and the first count is reset. The electro-kinetic system restarts (or the previous power level is returned) after the predetermined period. When the second count reaches a second count threshold (e.g., 3), the electro-kinetic system is shut-down until a reset condition is satisfied.

In accordance with an embodiment of the present invention, monitoring includes periodically sampling the current (or voltage) associated with the electro-kinetic system. These samples are compared to the threshold, which is a current threshold if a current is being sampled. This can alternatively be a voltage threshold if a voltage is being sampled. In accordance with an embodiment of the present inventions, a running average of the samples is produced and the running average is compared to the current or voltage threshold.

In accordance with an embodiment of the present invention, after the second count reaches the second count threshold, the electro-kinetic system remains shut-down until the second electrode is removed and replaced, or, until a power control switch is turned off and back on. In response to detecting removal and replacement of the second electrode, or turning off and on the power control switch, the first and second counts are reset and the electro-kinetic system is restarted. In accordance with an embodiment of the present invention, the first and second counts are reset when the sampled current (or voltage) does not exceed the threshold for an extended period (e.g., 60 seconds).

Embodiments of the present invention also provide systems and methods for compensating for variations in line voltages used to power an electro-kinetic air transporter and conditioner device. The electro-kinetic air transporter and conditioner device includes a high voltage generator that provides a potential difference between at least one emitter electrode and at least one collector electrode. The high voltage generator is driven by both a DC voltage obtained from an AC voltage source, and a low voltage pulse signal. The DC voltage is stepped down to produce a voltage sense signal indicative of a level of the AC voltage source. The voltage sense signal is monitored. At least one of a pulse width, duty cycle and frequency of the low voltage pulse signal is adjusted, based on the monitored voltage sense signal, in order to substantially maintain the potential difference at a desired level.

Other features and advantages of the invention will appear from the following description in which the preferred embodiments have been set forth in detail, in conjunction with the accompanying drawings and claims.

BRIEF DESCRIPTION OF THE FIGURES

FIG. 2A is a perspective view of an embodiment of the housing for the present invention; FIG. 2B is a perspective view of the embodiment shown in FIG. 2A, illustrating the removable array of second electrodes;

FIG. 3A is a perspective view of an embodiment of the present invention without a base; FIG. 3B is a top view of the embodiment of the present invention illustrated in FIG. 3A; FIG. 3C is a partial perspective view of the embodiment shown in FIGS. 3A–3B, illustrating the removable second array of electrodes; FIG. 3D is a side view of the embodiment of the present invention of FIG. 3A including a base; FIG. 3E is a perspective view of the embodiment in FIG. 3D, illustrating a removable rear panel which exposes a germicidal lamp;

FIG. 5A is a top, partial cross-sectioned view of an embodiment of the present invention, illustrating one configuration of the germicidal lamp; FIG. 5B is a top, partial cross-sectioned view of another embodiment of the present invention, illustrating another configuration of the germicidal lamp;

DETAILED DESCRIPTION OF THE PREFERRED EMBODIMENT

Figure 1:
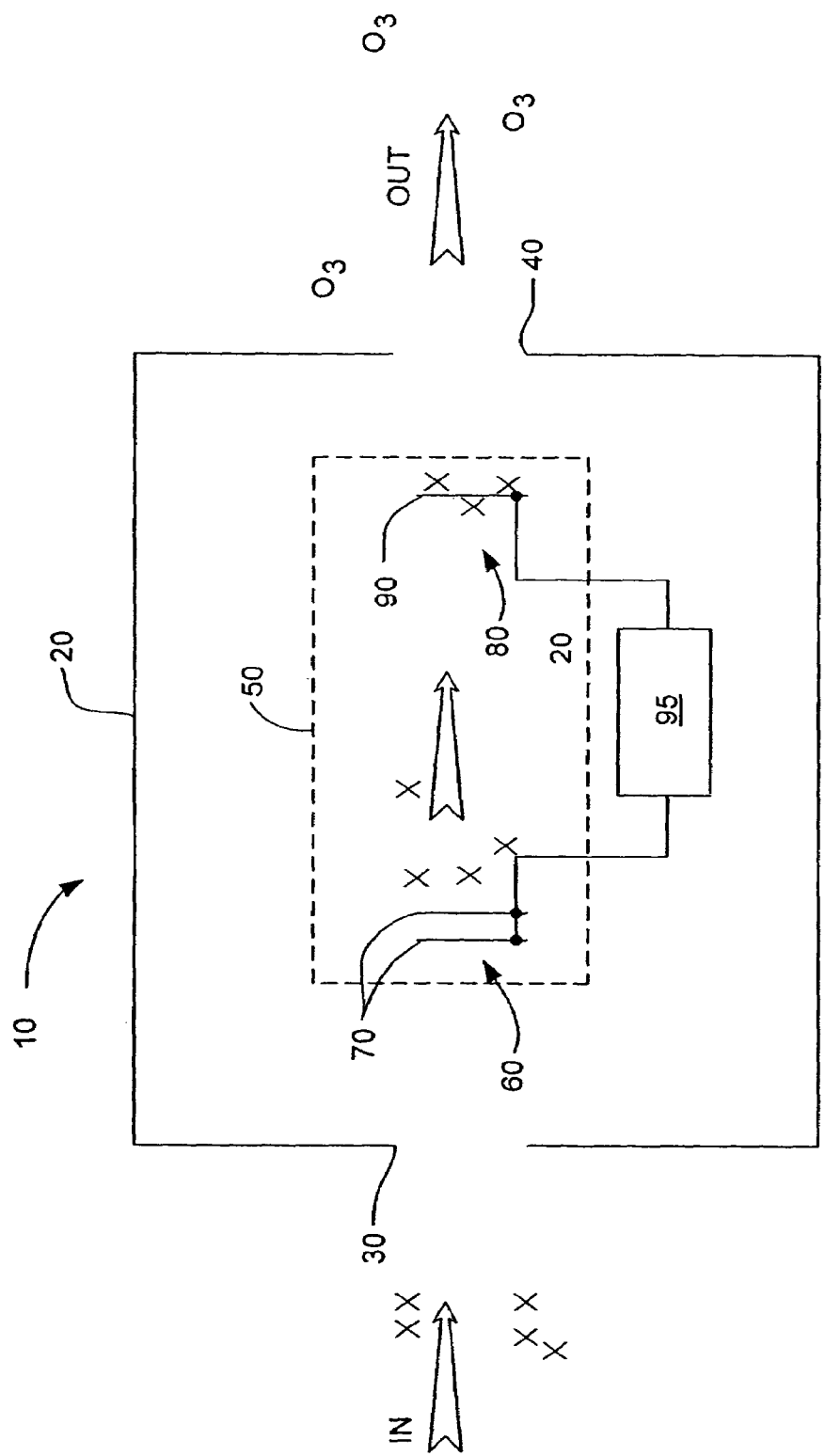
FIG. 1 depicts a generic electro-kinetic conditioner device that outputs ionized air and ozone, according to the prior art.
Figure 2A:
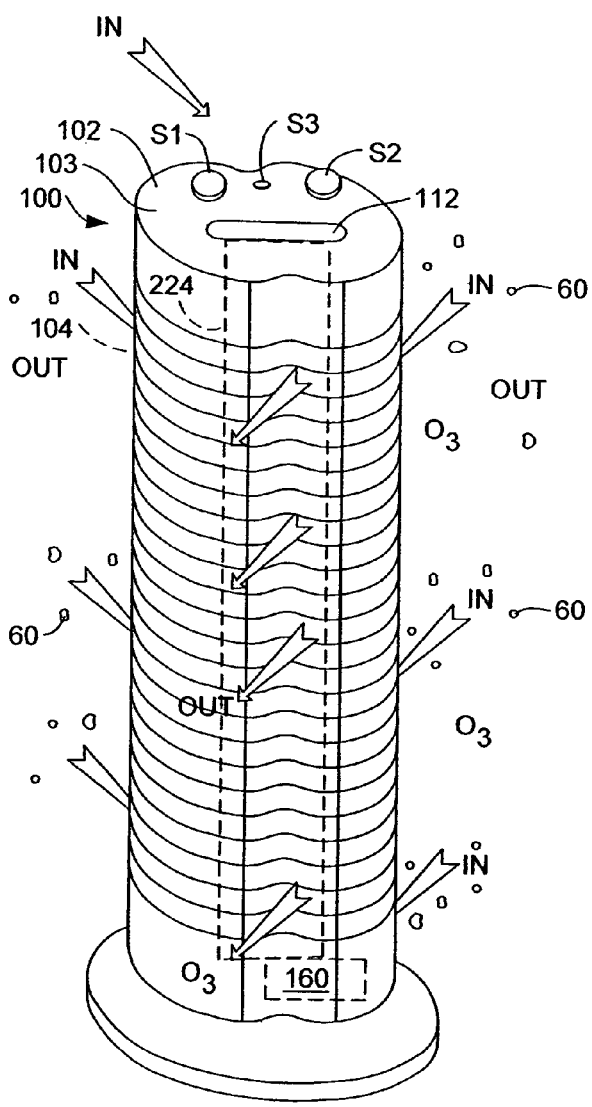
FIGS. 2A–2B.
Figure 2B:
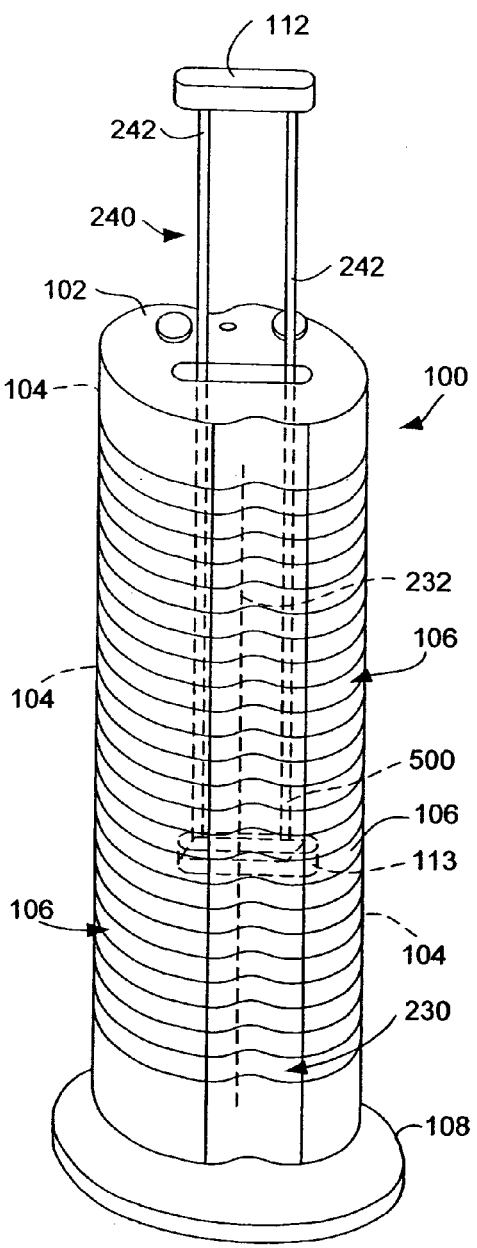

Overall Air Transporter-Conditioner System Configuration: FIGS. 2A–2B

FIGS. 2A–2B depicts a system which does not have incorporated therein a germicidal lamp. However, these embodiments do include other aspects such as the removable second electrodes which can be included in the other described embodiments.

FIGS. 2A and 2B depict an electro-kinetic air transporter-conditioner system 100 whose housing 102 includes preferably rear-located intake vents or louvers 104 and preferably front located exhaust vents 106, and a base pedestal 108. Preferably, the housing 102 is free standing and/or upstandingly vertical and/or elongated. Internal to the transporter housing 102 is an ion generating unit 160, preferably powered by an AC:DC power supply that is energizable or excitable using switch S1. Switch S1, along with the other below described user operated switches, are conveniently located at the top 103 of the unit 100. Ion generating unit 160 is self-contained in that other ambient air, nothing is required from beyond the transporter housing 102, save external operating potential, for operation of the present invention.

The upper surface 103 of the housing 102 includes a user-liftable handle member 112 to which is affixed a second array 240 of collector electrodes 242. The housing 102 also encloses a first array of emitter electrodes 230, or a single first emitter electrode shown here as a single wire or wire-shaped electrode 232. (The terms "wire" and "wire-shaped" shall be used interchangeably herein to mean an electrode either made from a wire or, if thicker or stiffer than a wire, having the appearance of a wire.) In the embodiment shown, handle member 112 lifts second array electrodes 240 upward causing the second electrode to telescope out of the top of the housing and, if desired, out of unit 100 for cleaning, while the first electrode array 230 remains within unit 100. As is evident from the figure, the second array of electrodes 240 can be lifted vertically out from the top 103 of unit 100 along the longitudinal axis or direction of the elongated housing 102. This arrangement with the second electrodes removable from the top 103 of the unit 100, makes it easy for the user to pull the second electrodes 242 out for cleaning. In FIG. 2B, the bottom ends of second electrodes 242 are connected to a member 113, to which is attached a mechanism 500, which includes a flexible member and a slot for capturing and cleaning the first electrode 232, whenever handle member 112 is moved upward or downward by a user. The first and second arrays of electrodes are coupled to the output terminals of ion generating unit 160.

The general shape of the embodiment of the invention shown in FIGS. 2A and 2B is that of a figure eight in cross-section, although other shapes are within the spirit and scope of the invention. The top-to-bottom height in one preferred embodiment is, 1 m, with a left-to-right width of preferably 15 cm, and a front-to-back depth of perhaps 10 cm, although other dimensions and shapes can of course be used. A louvered construction provides ample inlet and outlet venting in an ergonomical housing configuration. There need be no real distinction between vents 104 and 106, except their location relative to the second electrodes. These vents serve to ensure that an adequate flow of ambient air can be drawn into or made available to the unit 100, and that an adequate flow of ionized air that includes appropriate amounts of $O_3$ flows out from unit 100.

As will be described, when unit 100 is energized by depressing switch S1, high voltage or high potential output by an ion generator 160 produces ions at the first electrode 232, which ions are attracted to the second electrodes 242. The movement of the ions in an "IN" to "OUT" direction carries with the ions air molecules, thus electro-kinetically producing an outflow of ionized air. The "IN" rotation in FIGS. 2A and 2B denote the intake of ambient air with particulate matter 60. The "OUT" notation in the figures denotes the outflow of cleaned air substantially devoid of the particulate matter, which particulates matter adheres electrostatically to the surface of the second electrodes. In the process of generating the ionized airflow appropriate amounts of ozone ($O_3$) are beneficially produced. It may be desired to provide the inner surface of housing 102 with an electrostatic shield to reduce detectable electromagnetic radiation. For example, a metal shield could be disposed within the housing, or portions of the interior of the housing can be coated with a metallic paint to reduce such radiation.

Preferred Embodiments of Air-Transporter-Conditioner System with Germicidal Lamp FIGS. 3A–6 depict various embodiments of the device 200, with an improved ability to diminish or destroy microorganisms including bacteria, germs, and viruses. Specifically, FIGS. 3A–6 illustrate various preferred embodiments of the elongated and upstanding housing 210 with the operating controls located on the top surface 217 of the housing 210 for controlling the device 200.

FIGS. 3A–3E

Figure 3A:
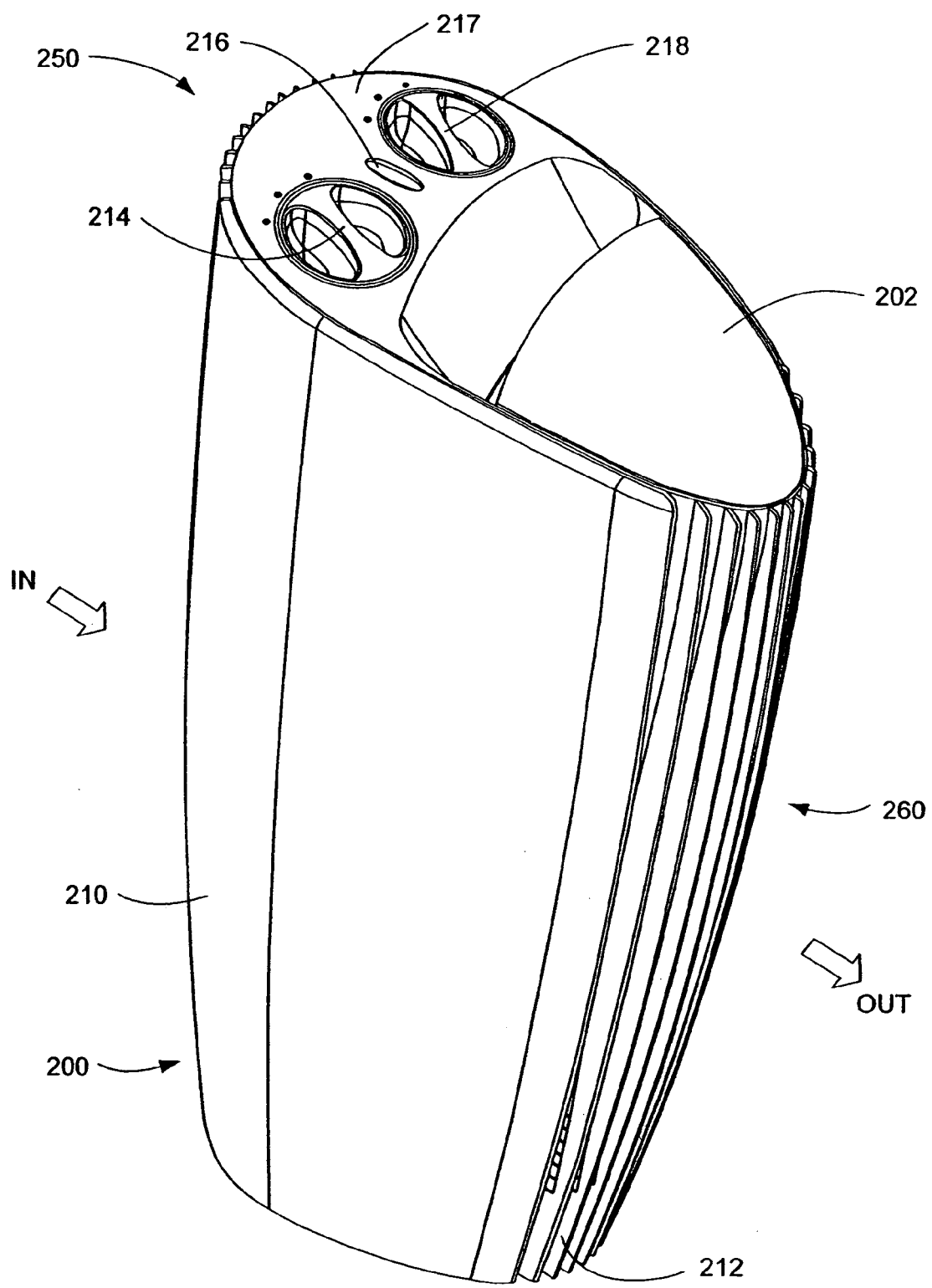
FIGS. 3A–3E.

FIG. 3A illustrates a first preferred embodiment of the housing 210 of device 200. The housing 210 is preferably made from a lightweight inexpensive material, ABS plastic for example. As a germicidal lamp (described hereinafter) is located within the housing 210, the material must be able to withstand prolonged exposure to class UV-C light. Non "hardened" material will degenerate over time if exposed to light such as UV-C. By way of example only, the housing 210 may be manufactured from CYCLOLAC® ABS Resin, (material designation VW300(f2)) which is manufactured by General Electric Plastics Global Products, and is certified by UL Inc. for use with ultraviolet light. It is within the scope of the present invention to manufacture the housing 210 from other UV appropriate materials.

In a preferred embodiment, the housing 210 is aerodynamically oval, elliptical, teardrop-shaped or egg-shaped. The housing 210 includes at least one air intake 250, and at least one air outlet 260. As used herein, it will be understood that the intake 250 is "upstream" relative to the outlet 260, and that the outlet 260 is "downstream" from the intake 250. "Upstream" and "downstream" describe the general flow of air into, through, and out of device 200, as indicated by the large hollow arrows.

Covering the inlet 250 and the outlet 260 are fins, louvers, or baffles 212. The fins 212 are preferably elongated and upstanding, and thus in the preferred embodiment, vertically oriented to minimize resistance to the airflow entering and exiting the device 200. Preferably the fins 212 are vertical and parallel to at least the second collector electrode array 240 (see FIG. 5A). The fins 212 can also be parallel to the first emitter electrode array 230. This configuration assists in the flow of air through the device 200 and also assists in preventing UV radiation from the UV or germicidal lamp 290 (described hereinafter), or other germicidal source, from exiting the housing 210. By way of example only, if the long width of the body from the inlet 250 to the outlet 260 is 8 inches, the collector electrode 242 (see FIG. 5A) can be 1¼" wide in the direction of airflow, and the fins 212 can be ¾" or ½" wide in the direction airflow. Of course, other proportionate dimensions are within the spirit and scope of the invention. Further, other fin and housing shapes which may not be as aerodynamic are within the spirit and scope of the invention.

From the above it is evident that preferably the cross-section of the housing 210 is oval, elliptical, teardrop-shaped or egg shaped with the inlet 250 and outlet 260 narrower than the middle (see line A—A in FIG. 5A) of the housing 210. Accordingly, the airflow, as it passes across line A—A, is slower due to the increased width and area of the housing 210. Any bacteria, germs, or virus within the airflow will have a greater dwell time and be neutralized by a germicidal device, such as, preferably, an ultraviolet lamp.

Figure 3B:
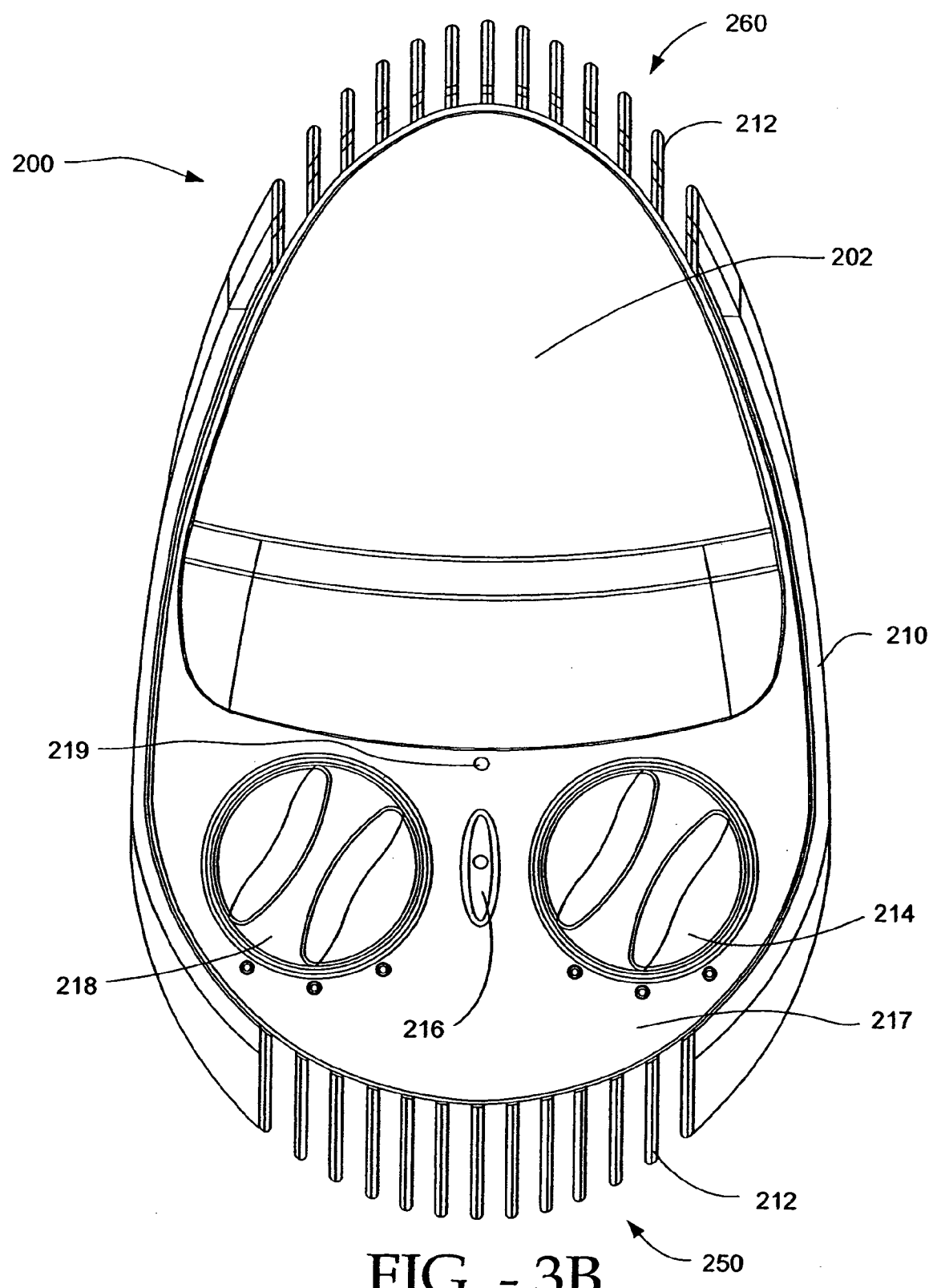

FIG. 3B illustrates the operating controls for the device 200. Located on top surface 217 of the housing 210 is an airflow speed control dial 214, a boost button 216, a function dial 218, and an overload/cleaning light 219. The airflow speed control dial 214 has three settings from which a user can choose: LOW, MED, and HIGH. The airflow rate is proportional to the voltage differential between the electrodes or electrode arrays coupled to the ion generator 160. The LOW, MED, and HIGH settings generate a different predetermined voltage difference between the first and second arrays. For example, the LOW setting will create the smallest voltage difference, while the HIGH setting will create the largest voltage difference. Thus, the LOW setting will cause the device 200 to generate the slowest airflow rate, while the HIGH setting will cause the device 200 to generate the fastest airflow rate. These airflow rates are created by the electronic circuit disclosed in FIGS. 7A–7B, and operate as disclosed below.

The function dial 218 enables a user to select "ON," "ON/GP," or "OFF." The unit 200 functions as an electrostatic air transporter-conditioner, creating an airflow from the inlet 250 to the outlet 260, and removing the particles within the airflow when the function dial 218 is set to the "ON" setting. The germicidal lamp 290 does not operate, or emit UV light, when the function dial 218 is set to "ON." The device 200 also functions as an electrostatic air transporter-conditioner, creating an airflow from the inlet 250 to the outlet 260, and removing particles within the airflow when the function dial 218 is set to the "ON/GP" setting. In addition, the "ON/GP" setting activates the germicidal lamp 290 to emit UV light to remove or kill bacteria within the airflow. The device 200 will not operate when the function dial 218 is set to the "OFF" setting.

As previously mentioned, the device 200 preferably generates small amounts of ozone to reduce odors within the room. If there is an extremely pungent odor within the room, or a user would like to temporarily accelerate the rate of cleaning, the device 200 has a boost button 216. When the boost button 216 is depressed, the device 200 will temporarily increase the airflow rate to a predetermined maximum rate, and generate an increased amount of ozone. The increased amount of ozone will reduce the odor in the room faster than if the device 200 was set to HIGH. The maximum airflow rate will also increase the particle capture rate of the device 200. In a preferred embodiment, pressing the boost button 216 will increase the airflow rate and ozone production continuously for 5 minutes. This time period may be longer or shorter. At the end of the preset time period (e.g., 5 minutes), the device 200 will return to the airflow rate previously selected by the control dial 214.

The overload/cleaning light 219 indicates if the second electrodes 242 require cleaning, or if arcing occurs between the first and second electrode arrays. The overload/cleaning light 219 may illuminate either amber or red in color. The light 219 will turn amber if the device 200 has been operating continuously for more than two weeks and the second array 240 has not been removed for cleaning within the two week period. The amber light is controlled by the below described micro-controller unit 130 (see FIG. 7). The device 200 will continue to operate after the light 219 turns amber. The light 219 is only an indicator. There are two ways to reset or turn the light 219 off. A user may remove and replace the second array 240 from the unit 200. The user may also turn the control dial 218 to the OFF position, and subsequently turn the control dial 218 back to the "ON" or "ON/GP" position. The MCU 130 will begin counting a new two week period upon completing either of these two steps.

The light 219 will turn red to indicate that continuous arcing has occurred between the first array 230 and the second array 240, as sensed by the MCU 130, which receives an arc sensing signal from the collector of an IGBT switch 126 shown in FIG. 7, described in more detail below. When continuous arcing occurs, the device 200 will automatically shut itself off. The device 200 cannot be restarted until the device 200 is reset. To reset the device 200, the second array 240 should first be removed from the housing 210 after the unit 200 is turned off. The second electrode 240 can then be cleaned and placed back into the housing 210. Then, the device 200 is turned on. If no arcing occurs, the device 200 will operate and generate an airflow. If the arcing between the electrodes continues, the device 200 will again shut itself off, and need to be reset.

Figure 3C:
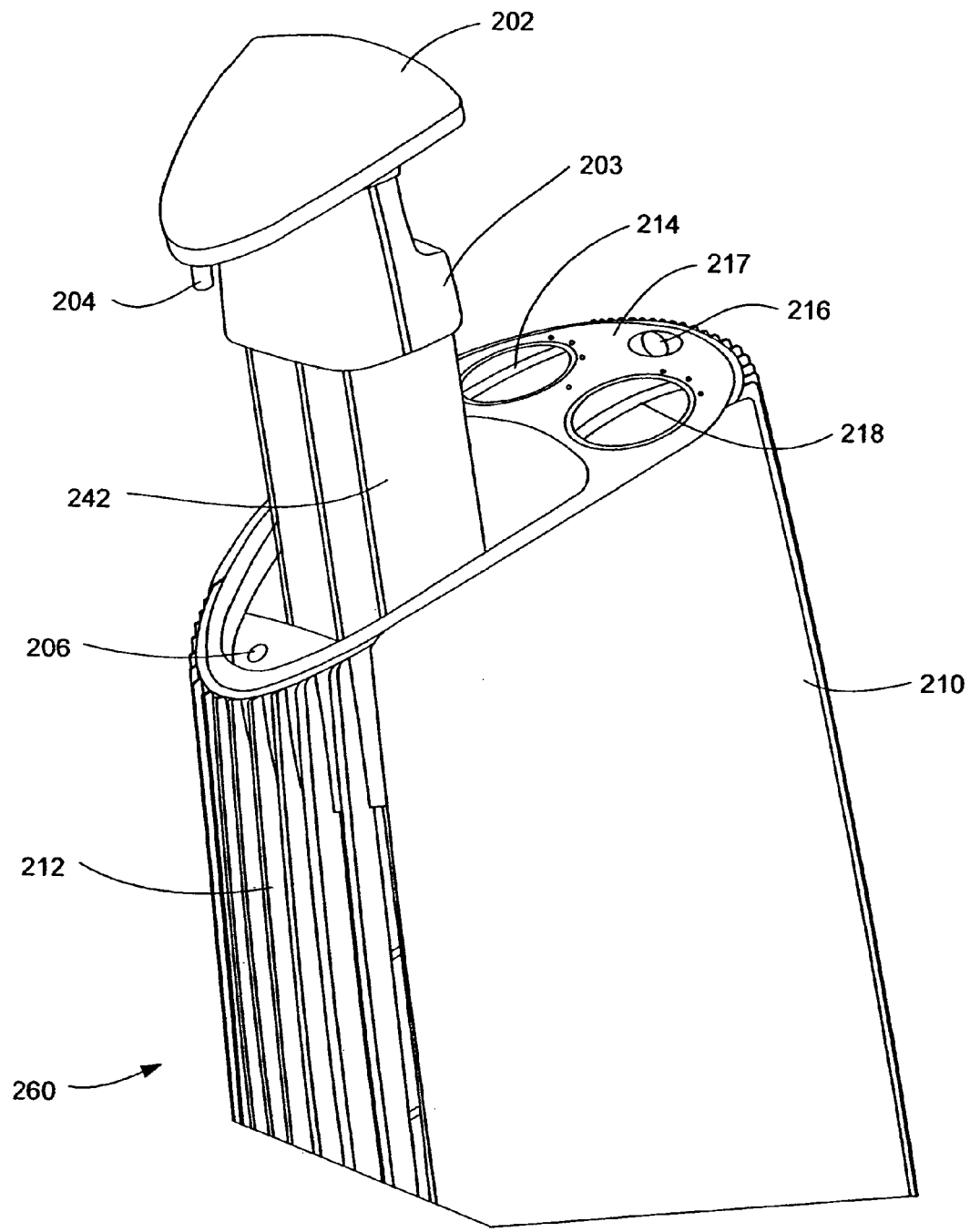

FIG. 3C illustrates the second electrodes 242 partially removed from the housing 210. In this embodiment, the handle 202 is attached to an electrode mounting bracket 203. The bracket 203 secures the second electrodes 242 in a fixed, parallel configuration. Another similar bracket 203 is attached to the second electrodes 242 substantially at the bottom (not shown). The two brackets 203 align the second electrodes 242 parallel to each other, and in-line with the airflow traveling through the housing 210. Preferably, the brackets 203 are non-conductive surfaces.

One of the various safety features can be seen with the second electrodes 242 partially removed. As shown in FIG. 3C, an interlock post 204 extends from the bottom of the handle 202. When the second electrodes 242 are placed completely into the housing 210, the handle 202 rests within the top surface 217 of the housing, as shown by FIGS. 3A–3B. In this position, the interlock post 204 protrudes into the interlock recess 206 and activates a switch connecting the electrical circuit of the unit 200. When the handle 202 is removed from the housing 210, the interlock post 204 is pulled out of the interlock recess 206 and the switch opens the electrical circuit. With the switch in an open position, the unit 200 will not operate. Thus, if the second electrodes 242 are removed from the housing 210 while the unit 200 is operating, the unit 200 will shut off as soon as the interlock post 204 is removed from the interlock recess 206.

Figure 3D:
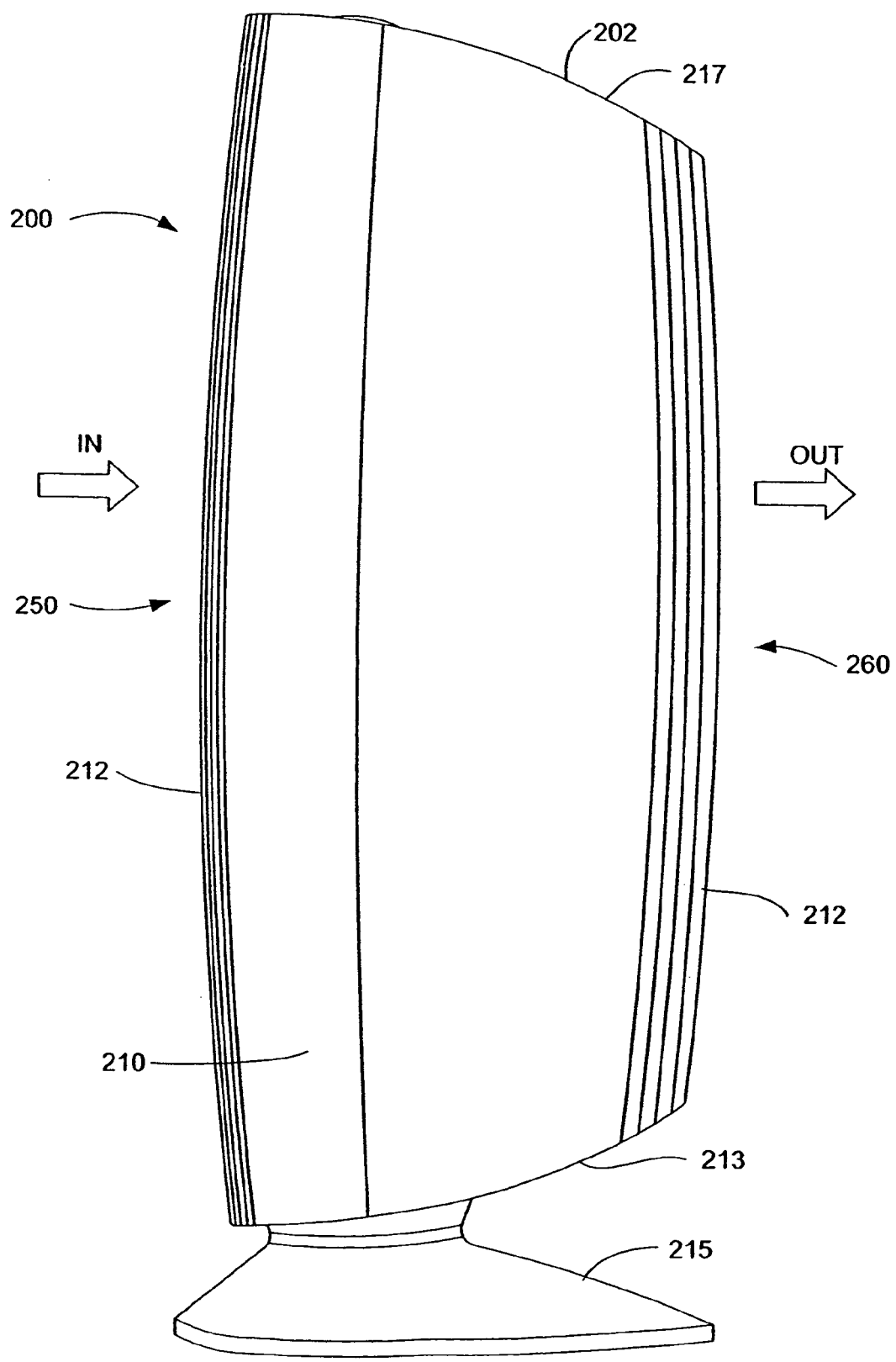

FIG. 3D depicts the housing 210 mounted on a stand or base 215. The housing 210 has an inlet 250 and an outlet 260. The base 215 sits on a floor surface. The base 215 allows the housing 210 to remain in a vertical position. It is within the scope of the present invention for the housing 210 to be pivotally connected to the base 215. As can be seen in FIG. 3D, housing 210 includes sloped top surface 217 and sloped bottom surface 213. These surfaces slope inwardly from inlet 250 to outlet 260 to additionally provide a streamline appearance and effect.

Figure 3E:
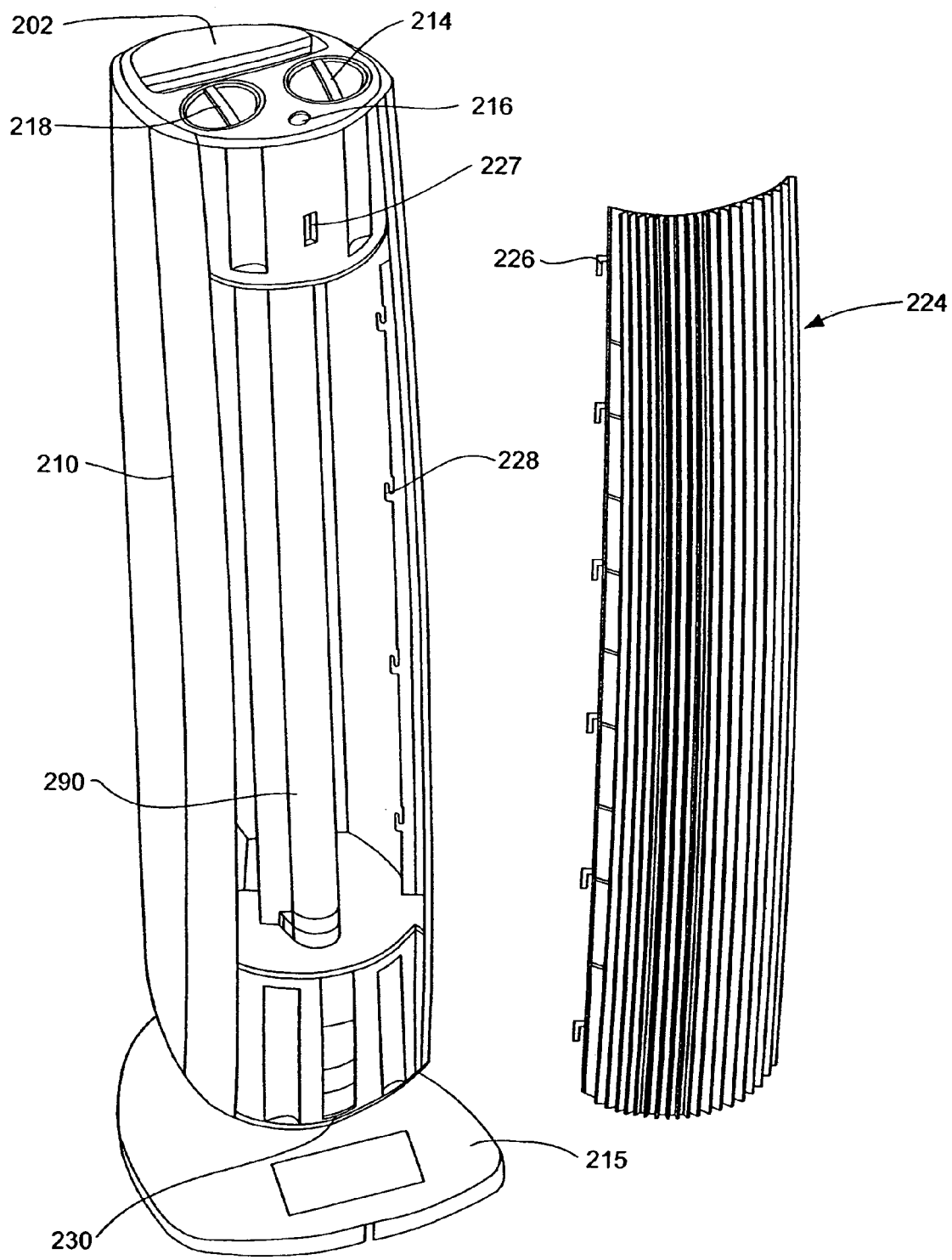

FIG. 3E illustrates that the housing 210 has a removable rear panel 224, allowing a user to easily access and remove the germicidal lamp 290 from the housing 210 when the lamp 290 expires. This rear panel 224 in this embodiment defines the air inlet and comprises the vertical louvers. The rear panel 224 has locking tabs 226 located on each side, along the entire length of the panel 224. The locking tabs 226, as shown in FIG. 3E, are "L"-shaped. Each tab 224 extends away from the panel 224, inward towards the housing 210, and then projects downward, parallel with the edge of the panel 224. It is within the spirit and scope of the invention to have differently shaped tabs 226. Each tab 224 individually and slidably interlocks with recesses 228 formed within the housing 210. The rear panel 224 also has a biased lever (not shown) located at the bottom of the panel 224 that interlocks with the recess 230. To remove the panel 224 from the housing 210, the lever is urged away from the housing 210, and the panel 224 is slid vertically upward until the tabs 226 disengage the recesses 228. The panel 224 is then pulled away from the housing 210. Removing the panel 224 exposes the lamp 290 for replacement.

The panel 224 also has a safety mechanism to shut the device 200 off when the panel 224 is removed. The panel 224 has a rear projecting tab (not shown) that engages the safety interlock recess 227 when the panel 224 is secured to the housing 210. By way of example only, the rear tab depresses a safety switch located within the recess 227 when the rear panel 224 is secured to the housing 210. The device 200 will operate only when the rear tab in the panel 224 is fully inserted into the safety interlock recess 227. When the panel 224 is removed from the housing 210, the rear projecting tab is removed from the recess 227 and the power is cut-off to the entire device 200. For example if a user removes the rear panel 224 while the device 200 is running, and the germicidal lamp 290 is emitting UV radiation, the device 200 will turn off as soon as the rear projecting tab disengages from the recess 227. Preferably, the device 200 will turn off when the rear panel 224 is removed only a very short distance (e.g., ¼") from the housing 210. This safety switch operates very similar to the interlocking post 204, as shown in FIG. 3C.

FIG. 4

Figure 4:
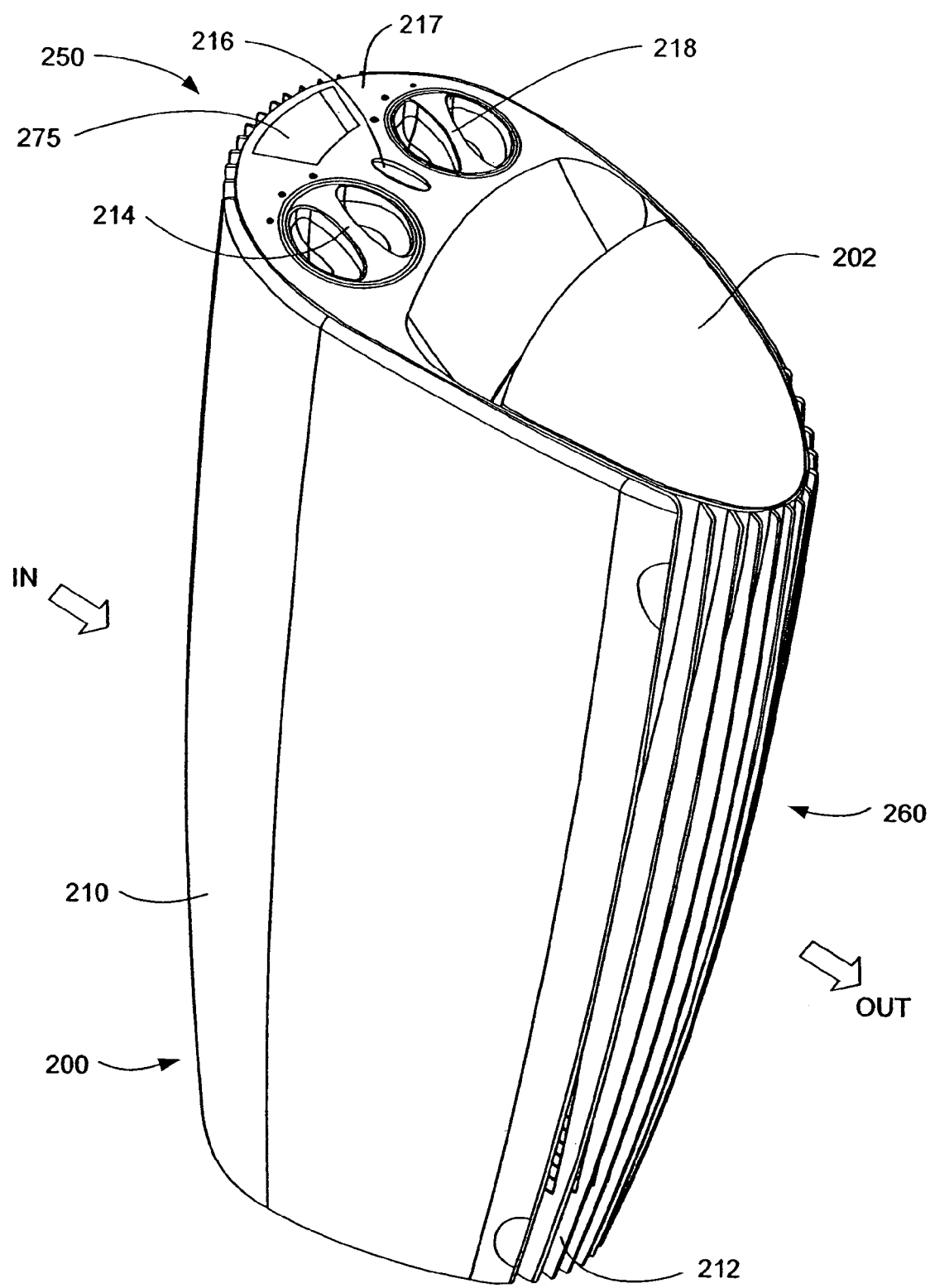
FIG. 4 is a perspective view of another embodiment of the present invention.

FIG. 4 illustrates yet another embodiment of the housing 210. In this embodiment, the germicidal lamp 290 may be removed from the housing 210 by lifting the germicidal lamp 290 out of the housing 210 through the top surface 217. The housing 210 does not have a removable rear panel 224. Instead, a handle 275 is affixed to the germicidal lamp 290. The handle 275 is recessed within the top surface 217 of the housing 210 similar to the handle 202, when the lamp 290 is within the housing 210. To remove the lamp 290, the handle 275 is vertically raised out of the housing 210.

The lamp 290 is situated within the housing 210 in a similar manner as the second array of electrodes 240. That is to say, that when the lamp 290 is pulled vertically out of the top 217 of the housing 210, the electrical circuit that provides power to the lamp 290 is disconnected. The lamp 290 is mounted in a lamp fixture that has circuit contacts which engages the circuit in FIG. 7A. As the lamp 290 and fixture are pulled out, the circuit contacts are disengaged. Further, as the handle 275 is lifted from the housing 210, a cutoff switch will shut the entire device 200 off. This safety mechanism ensures that the device 200 will not operate without the lamp 290 placed securely in the housing 210, preventing an individual from directly viewing the radiation emitted from the lamp 290. Reinserting the lamp 290 into the housing 210 causes the lamp fixture to re-engage the circuit contacts as is known in the art. In similar, but less convenient fashion, the lamp 290 may be designed to be removed from the bottom of the housing 210.

The germicidal lamp 290 is a preferably UV-C lamp that preferably emits viewable light and radiation (in combination referred to as radiation or light 280) having wavelength of about 254 nm. This wavelength is effective in diminishing or destroying bacteria, germs, and viruses to which it is exposed. Lamps 290 are commercially available. For example, the lamp 290 may be a Phillips model TUV 15W/G15 T8, a 15 W tubular lamp measuring about 25 mm in diameter by about 43 cm in length. Another suitable lamp is the Phillips TUV 8WG8 T6, an 8 W lamp measuring about 15 mm in diameter by about 29 cm in length. Other lamps that emit the desired wavelength can instead be used.

FIGS. 5A–5B

Figure 5A:
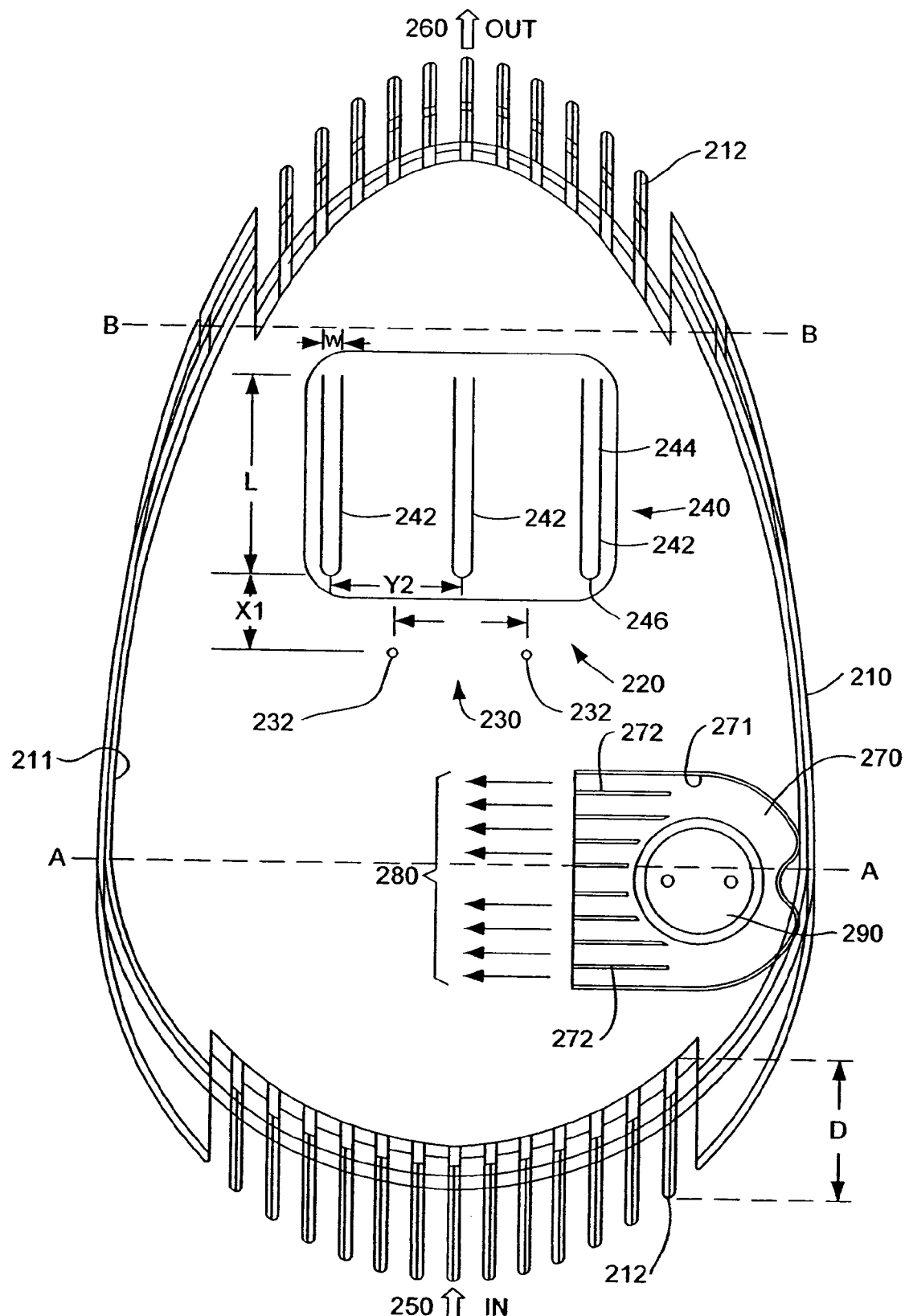
FIGS. 5A–5B.
Figure 5B:
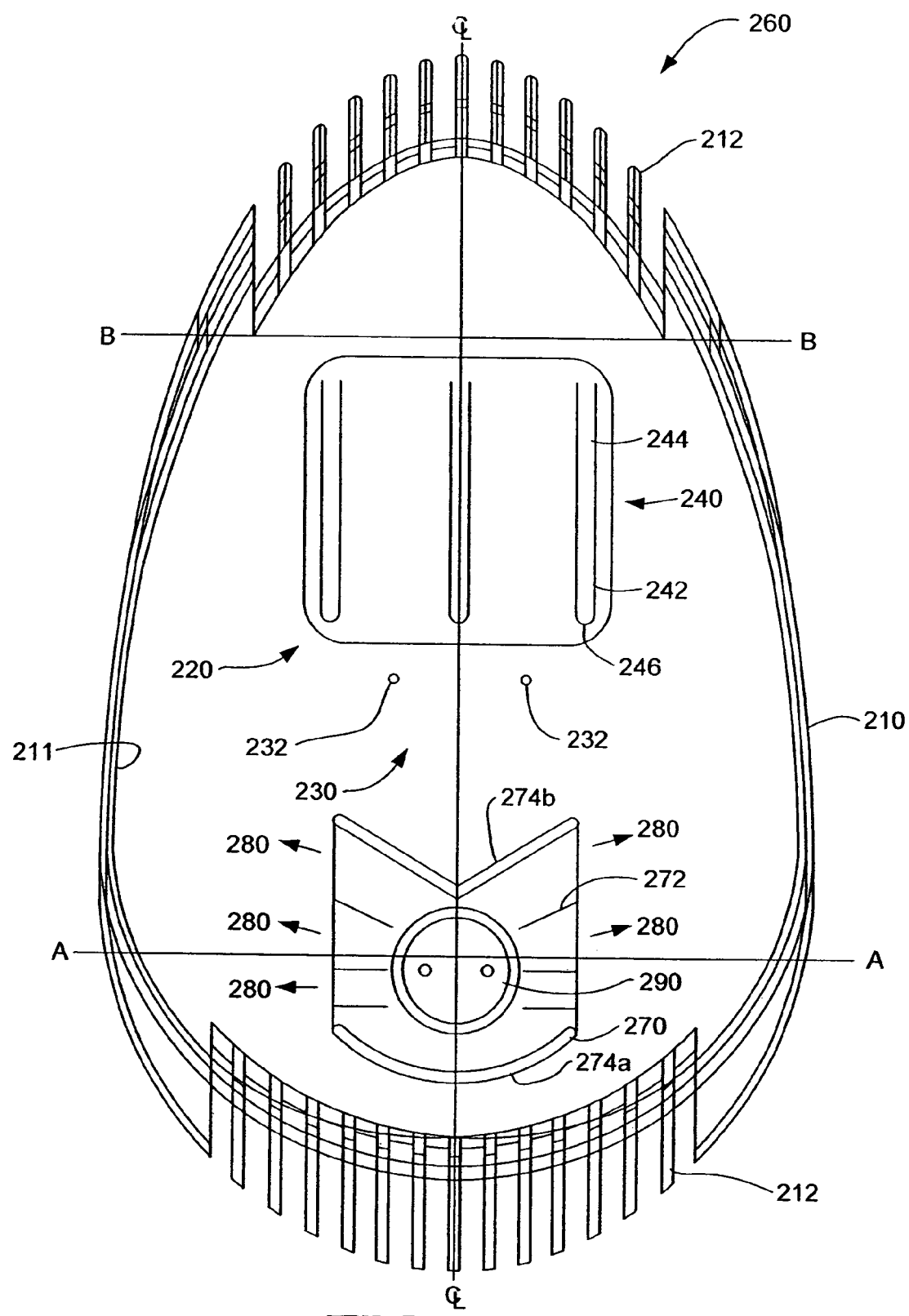

As previously mentioned, one role of the housing 210 is to prevent an individual from viewing, by way of example, ultraviolet (UV) radiation generated by a germicidal lamp 290 disposed within the housing 210. FIGS. 5A–5B illustrate preferred locations of the germicidal lamp 290 within the housing 210. FIGS. 5A–5B further show the spacial relationship between the germicidal lamp 290 and the electrode assembly 220, and the germicidal lamp 290 and the inlet 250 and the outlet 260 and the inlet and outlet louvers.

In a preferred embodiment, the inner surface 211 of the housing 210 diffuses or absorbs the UV light emitted from the lamp 290. FIGS. 5A–5B illustrate that the lamp 290 does emit some light 280 directly onto the inner surface 211 of the housing 210. By way of example only, the inner surface 211 of the housing 210 can be formed with a non-smooth finish, or a non-light reflecting finish or color, to also prevent the UV-C radiation from exiting through either the inlet 250 or the outlet 260. The UV portion of the radiation 280 striking the wall 211 will be absorbed and disbursed as indicated above.

As discussed above, the fins 212 covering the inlet 250 and the outlet 260 also limit any line of sight of the user into the housing 210. The fins 212 are vertically oriented within the inlet 250 and the outlet 260. The depth D of each fin 212 is preferably deep enough to prevent an individual from directly viewing the interior wall 211. In a preferred embodiment, an individual cannot directly view the inner surface 211 by moving from side-to-side, while looking into the outlet 260 or the inlet 250. Looking between the fins 212 and into the housing 210 allows an individual to "see through" the device 200. That is, a user can look into the inlet vent 250 or the outlet vent 260 and see out of the other vent. It is to be understood that it is acceptable to see light or a glow coming from within housing 210, if the light has a non-UV wavelength that is acceptable for viewing. In general, an user viewing into the inlet 250 or the outlet 260 may be able to notice a light or glow emitted from within the housing 210. This light is acceptable to view. In general, when the radiation 280 strikes the interior surface 211 of the housing 210, the radiation 280 is shifted from its UV spectrum. The wavelength of the radiation changes from the UV spectrum into an appropriate viewable spectrum. Thus, any light emitted from within the housing 210 is appropriate to view.

As also discussed above, the housing 210 is designed to optimize the reduction of microorganisms within the airflow. The efficacy of radiation 280 upon microorganisms depends upon the length of time such organisms are subjected to the radiation 280. Thus, the lamp 290 is preferably located within the housing 210 where the airflow is the slowest. In preferred embodiments, the lamp 290 is disposed within the housing 210 along line A—A (see FIGS. 5A–7). Line A—A designates the largest width and cross-sectional area of the housing 210, perpendicular to the airflow. The housing 210 creates a fixed volume for the air to pass through. In operation, air enters the inlet 250, which has a smaller width, and cross-sectional area, than along line A—A. Since the width and cross-sectional area of the housing 210 along line A—A are larger than the width and cross-sectional area of the inlet 250, the airflow will decelerate from the inlet 250 to the line A—A. By placing the lamp 290 substantially along line A—A, the air will have the longest dwell time as it passes through the radiation 280 emitted by the lamp 290. In other words, the microorganisms within the air will be subjected to the radiation 280 for the longest period possible by placing the lamp 290 along line A—A. It is, however, within the scope of the present invention to locate the lamp 290 anywhere within the housing 210, preferably upstream of the electrode assembly 220.

A shell or housing 270 substantially surrounds the lamp 290. The shell 270 prevents the light 280 from shining directly towards the inlet 250 or the outlet 260. In a preferred embodiment, the interior surface of the shell 270 that faces the lamp 290 is a non-reflective surface. By way of example only, the interior surface of the shell 270 may be a rough surface, or painted a dark, non-gloss color such as black. The lamp 290, as shown in FIGS. 5A–5B, is a circular tube parallel to the housing 210. In a preferred embodiment, the lamp 290 is substantially the same length as, or shorter than, the fins 212 covering the inlet 250 and outlet 260. The lamp 290 emits the light 280 outward in a 360° pattern. The shell 270 blocks the portion of the light 280 emitted directly towards the inlet 250 and the outlet 260. As shown in FIGS. 5A and 5B, there is no direct line of sight through the inlet 250 or the outlet 260 that would allow a person to view the lamp 290. Alternatively, the shell 270 can have an internal reflective surface in order to reflect radiation into the air stream.

In the embodiment shown in FIG. 5A, the lamp 290 is located along the side of the housing 210 and near the inlet 250. After the air passes through the inlet 250, the air is immediately exposed to the light 280 emitted by the lamp 290. An elongated "U"-shaped shell 270 substantially encloses the lamp 290. The shell 270 has two mounts to support and electrically connect the lamp 290 to the power supply.

In a preferred embodiment, as shown in FIG. 5B, the shell 270 comprises two separate surfaces. The wall 274a is located between the lamp 290 and the inlet 250. The first wall 274a is preferably "U"-shaped, with the concave surface facing the lamp 290. The convex surface of the wall 274a is preferably a non-reflective surface. Alternatively, the convex surface of the wall 274a may reflect the light 280 outward toward the passing airflow. The wall 274a is integrally formed with the removable rear panel 224. When the rear panel 224 is removed from the housing 210, the wall 274a is also removed, exposing the germicidal lamp 290. The germicidal lamp 290 is easily accessible in order to, as an example, replace the lamp 290 when it expires.

The wall 274b, as shown in FIG. 5B, is "V"-shaped. The wall 274b is located between the lamp 290 and the electrode assembly 220 to prevent a user from directly looking through the outlet 260 and viewing the UV radiation emitted from the lamp 290. In a preferred embodiment, the wall 274b is also a non-reflective surface. Alternatively, the wall 274b may be a reflective surface to reflect the light 280. It is within the scope of the present invention for the wall 274b to have other shapes such as, but not limited to, "U"-shaped or "C"-shaped.

The shell 270 may also have fins 272. The fins 272 are spaced apart and preferably substantially perpendicular to the passing airflow. In general, the fins 272 further prevent the light 280 from shining directly towards the inlet 250 and the outlet 260. The fins have a black or non-reflective surface. Alternatively, the fins 272 may have a reflective surface. Fins 272 with a reflective surface may shine more light 280 onto the passing airflow because the light 280 will be repeatedly reflected and not absorbed by a black surface. The shell 270 directs the radiation towards the fins 272, maximizing the light emitted from the lamp 290 for irradiating the passing airflow. The shell 270 and fins 272 direct the radiation 280 emitted from the lamp 290 in a substantially perpendicular orientation to the crossing airflow traveling through the housing 210. This prevents the radiation 280 from being emitted directly towards the inlet 250 or the outlet 260.

FIG. 6

Figure 6:
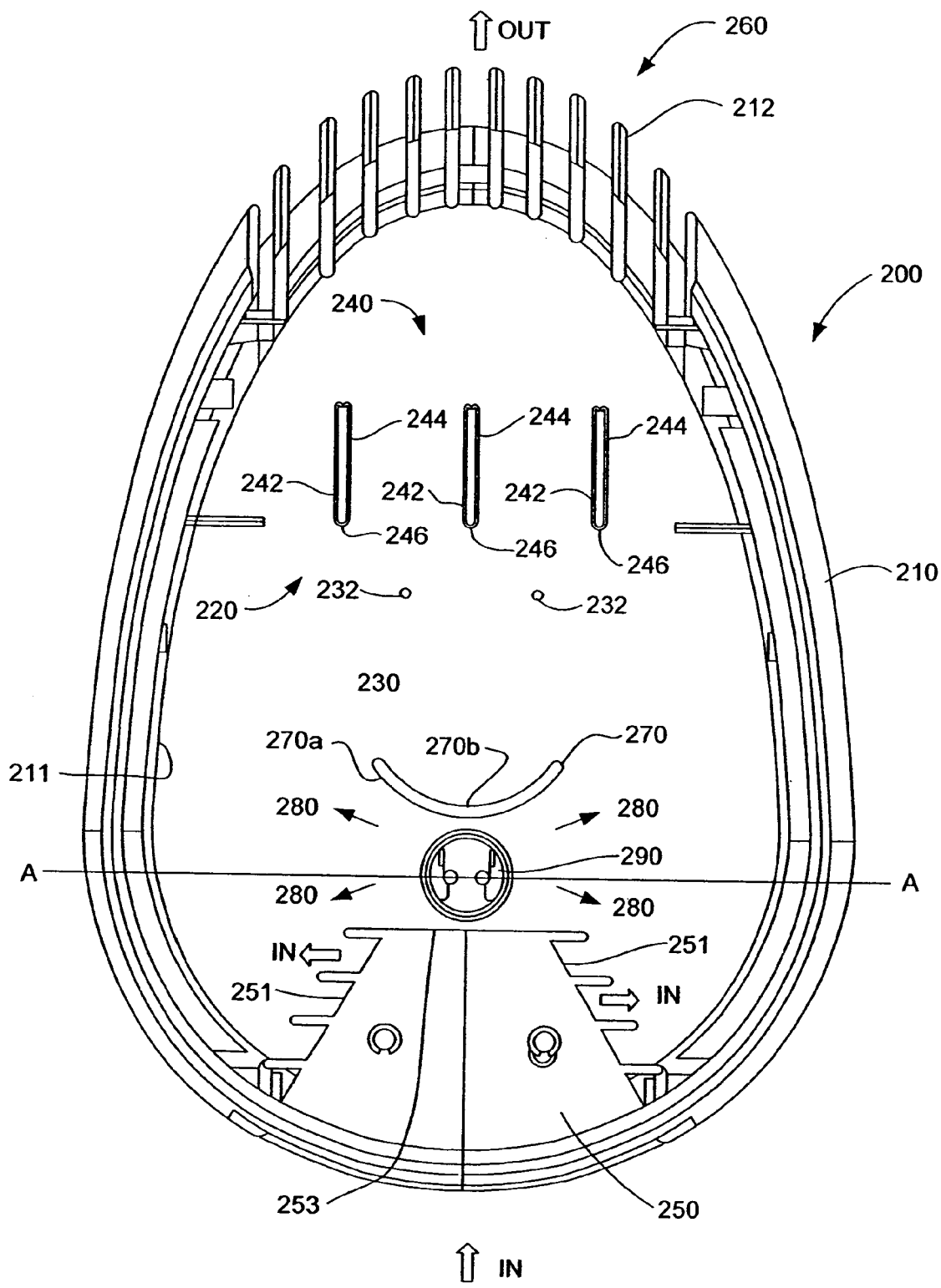
FIG. 6 is a top, partial cross-sectional view of yet another embodiment of the present invention.

FIG. 6 illustrates yet another embodiment of the device 200. The embodiment shown in FIG. 6 is a smaller, more portable, desk version of the air transporter-conditioner. Air is brought into the housing 210 through the inlet 250, as shown by the arrows marked "IN." The inlet 250 in this embodiment is an air chamber having multiple vertical slots 251 located along each side. In this embodiment, the slots are divided across the direction of the airflow into the housing 210. The slots 251 preferably are spaced apart a similar distance as the fins 212 in the previously described embodiments, and are substantially the same height as the side walls of the air chamber. In operation, air enters the housing 210 by entering the chamber 250 and then exiting the chamber 250 through the slots 251. The air contacts the interior wall 211 of the housing 210 and continues to travel through the housing 210 towards the outlet 260. Since the rear wall 253 of the chamber is a solid wall, the device 200 only requires a single non-reflective housing 270 located between the germicidal lamp 290 and the electrode assembly 220 and the outlet 260. The housing 270 in FIG. 6 is preferably "U"-shaped, with the convex surface 270a facing the germicidal lamp 290. The surface 270a directs the light 280 toward the interior surface 211 of the housing 210 and maximizes the disbursement of radiation into the passing airflow. It is within the scope of the invention for the surface 270 to comprise other shapes such as, but not limited to, a "V"-shaped surface, or to have the concave surface 270b face the lamp 290. Also in other embodiments the housing 270 can have a reflective surface in order to reflect radiation into the air stream. Similar to the previous embodiments, the air passes the lamp 290 and is irradiated by the light 280 soon after the air enters the housing 210, and prior to reaching the electrode assembly 220.

FIGS. 5A–6 illustrate embodiments of the electrode assembly 220. The electrode assembly 220 comprises a first emitter electrode array 230 and a second particle collector electrode array 240, which is preferably located downstream of the germicidal lamp 290. The specific configurations of the electrode array 220 are discussed below, and it is to be understood that any of the electrode assembly configurations discussed below may be used in the device depicted in FIGS. 2A–6. It is the electrode assembly 220 that creates ions and causes the air to flow electro-kinetically between the first emitter electrode array 230 and the second collector electrode array 240. In the embodiments shown in FIG. 5A–6, the first array 230 comprises two wire-shaped electrodes 232, while the second array 240 comprises three "U"-shaped electrodes 242. Each "U"-shaped electrode has a nose 246 and two trailing sides 244. It is within the scope of the invention for the first array 230 and the second array 240 to include electrodes having other shapes as mentioned above and described below.

Electrical Circuit for the Electro-Kinetic Device:

FIG. 7

Figure 7:
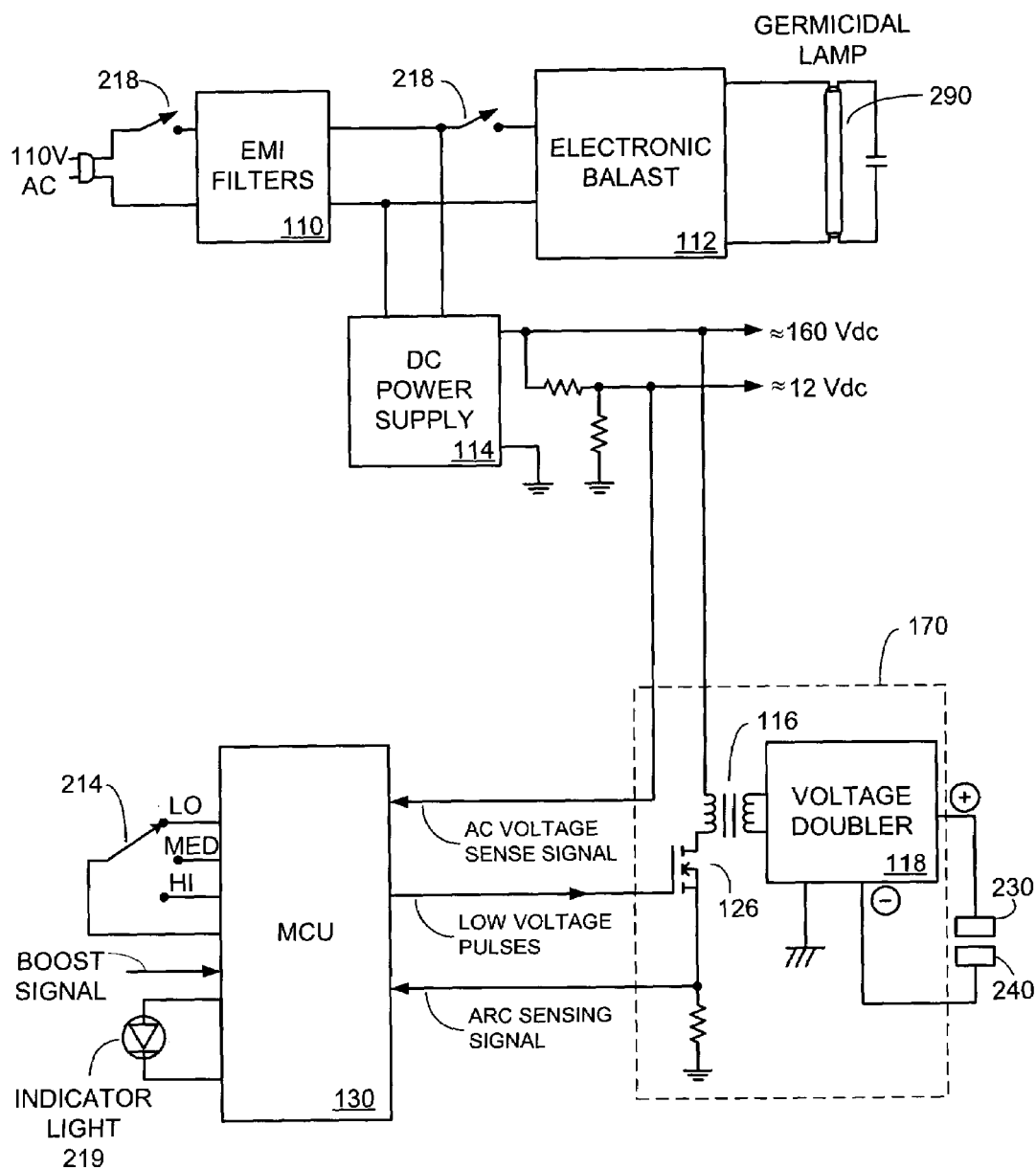
FIG. 7 is an electrical block diagram of an embodiment of a circuit of the present invention.

FIG. 7 illustrates an electrical block diagram for the electro-kinetic device 200, according to an embodiment of the present invention. The device 200 has an electrical power cord that plugs into a common electrical wall socket that provides a nominal 110VAC. An electromagnetic interference (EMI) filter 110 is placed across the incoming nominal 110VAC line to reduce and/or eliminate high frequencies generated by the various circuits within the device 200, such as an electronic ballast 112. The electronic ballast 112 is electrically connected to the germicidal lamp 290 to regulate, or control, the flow of current through the lamp 290. A switch 218 is used to turn the lamp 290 on or off. Electrical components such as the EMI Filter 110 and electronic ballast 112 are well known in the art and do not require a further description.

A DC Power Supply 114 is designed to receive the incoming nominal 110VAC and to output a first DC voltage (e.g., 160VDC) for the high voltage generator 170. The first DC voltage (e.g., 160VDC) is also stepped down through a resistor network to a second DC voltage (e.g., about 12VDC) that the micro-controller unit (MCU) 130 can monitor without being damaged. The MCU 130 can be, for example, a Motorola 68HC908 series micro-controller, available from Motorola. In accordance with an embodiment of the present invention, the MCU 130 monitors the stepped down voltage (e.g., about 12VDC), which is labeled the AC voltage sense signal in FIG. 7, to determine if the AC line voltage is above or below the nominal 110VAC, and to sense changes in the AC line voltage. For example, if a nominal 110VAC increases by 10% to 121VAC, then the stepped down DC voltage will also increase by 10%. The MCU 130 can sense this increase and then reduce the pulse width, duty cycle and/or frequency of the low voltage pulses to maintain the output power (provided to the high voltage generator 170) to be the same as when the line voltage is at 110VAC. Conversely, when the line voltage drops, the MCU 130 can sense this decrease and appropriately increase the pulse width, duty cycle and/or frequency of the low voltage pulses to maintain a constant output power. Such voltage adjustment features of the present invention also enable the same unit 200 to be used in different countries that have different nominal voltages than in the United States (e.g., in Japan the nominal AC voltage is 100VAC).

The high voltage pulse generator 170 is coupled between the first electrode array 230 and the second electrode array 240, to provide a potential difference between the arrays. Each array can include one or more electrodes. The high voltage pulse generator 170 may be implemented in many ways. In the embodiment shown, the high voltage pulse generator 170 includes an electronic switch 126, a step-up transformer 116 and a voltage doubler 118. The primary side of the step-up transformer 116 receives the first DC voltage (e.g., 160VDC) from the DC power supply. An electronic switch receives low voltage pulses (of perhaps 20–25 KHz frequency) from the micro-controller unit (MCU) 130. Such a switch is shown as an insulated gate bipolar transistor (IGBT) 126. The IGBT 126, or other appropriate switch, couples the low voltage pulses from the MCU 130 to the input winding of the step-up transformer 116. The secondary winding of the transformer 116 is coupled to the voltage doubler 118, which outputs the high voltage pulses to the first and second electrode arrays 230 and 240. In general, the IGBT 126 operates as an electronic on/off switch. Such a transistor is well known in the art and does not require a further description.

When driven, the generator 170 receives the low input DC voltage (e.g., 160VDC) from the DC power supply 114 and the low voltage pulses from the MCU 130, and generates high voltage pulses of preferably at least 5 KV peak-to-peak with a repetition rate of about 20 to 25 KHz. Preferably, the voltage doubler 118 outputs about 6 to 9KV to the first array 230, and about 12 to 18KV to the second array 240. It is within the scope of the present invention for the voltage doubler 118 to produce greater or smaller voltages. The high voltage pulses preferably have a duty cycle of about 10%–15%, but may have other duty cycles, including a 100% duty cycle.

The MCU 130 receives an indication of whether the control dial 214 is set to the LOW, MEDUM or HIGH airflow setting. The MCU 130 controls the pulse width, duty cycle and/or frequency of the low voltage pulse signal provided to switch 126, to thereby control the airflow output of the device 200, based on the setting of the control dial 214. To increase the airflow output, the MCU 130 can increase the pulse width, frequency and/or duty cycle. Conversely, to decrease the airflow output rate, the MCU 130 can reduce the pulse width, frequency and/or duty cycle. In accordance with an embodiment, the low voltage pulse signal (provided from the MCU 130 to the high voltage generator 170) can have a fixed pulse width, frequency and duty cycle for the LOW setting, another fixed pulse width, frequency and duty cycle for the MEDIUM setting, and a further fixed pulse width, frequency and duty cycle for the HIGH setting. However, depending on the setting of the control dial 214, the above described embodiment may produce too much ozone (e.g., at the HIGH setting) or too little airflow output (e.g., at the LOW setting). According, a more elegant solution, described below, is preferred.

In accordance with an embodiment of the present invention, the low voltage pulse signal created by the MCU 130 modulates between a "high" airflow signal and a "low" airflow signal, with the control dial setting specifying the durations of the "high" airflow signal and/or the "low" airflow signal. This will produce an acceptable airflow output, while limiting ozone production to acceptable levels, regardless of whether the control dial 214 is set to HIGH, MEDIUM or LOW. For example, the "high" airflow signal can have a pulse width of 5 microseconds and a period of 40 microseconds (i.e., a 12.5% duty cycle), and the "low" airflow signal can have a pulse width of 4 microseconds and a period of 40 microseconds (i.e., a 10% duty cycle). When the control dial 214 is set to HIGH, the MCU 130 outputs a low voltage pulse signal that modulates between the "low" airflow signal and the "high" airflow signal, with, for example, the "high" airflow signal being output for 2.0 seconds, followed by the "low" airflow signal being output for 8.0 second. When the control dial 214 is set to MEDIUM, the "low" airflow signal can be increased to, for example, 16 seconds (e.g., the low voltage pulse signal will include the "high" airflow signal for 2.0 seconds, followed by the "low" airflow signal for 16 seconds). When the control dial 214 is set to LOW, the "low" airflow signal can be further increased to, for example, 24 seconds (e.g., the low voltage pulse signal will include a "high" airflow signal for 2.0 seconds, followed by the "low" airflow signal for 24 seconds).

Alternatively, or additionally, the frequency of the low voltage pulse signal (used to drive the transformer 116) can be adjusted to distinguish between the LOW, MEDIUM and HIGH settings.

In accordance with another embodiment of the present invention, when the control dial 214 is set to HIGH, the electrical signal output from the MCU 130, modulating between the "high" and "low" airflow signals, will continuously drive the high voltage generator 170. When the control dial 214 is set to MEDIUM, the electrical signal output from the MCU 130 will cyclically drive the high voltage generator 170 for a predetermined amount of time (e.g., 25 seconds), and then drop to a zero or a lower voltage for a further predetermined amount of time (e.g., a further 25 seconds). Thus, the overall airflow rate through the device 200 is slower when the dial 214 is set to MEDIUM than when the control dial 214 is set to HIGH. When the control dial 214 is set to LOW, the signal from the MCU 130 will cyclically drive the high voltage generator 170 for a predetermined amount of time (e.g., 25 seconds), and then drop to a zero or a lower voltage for a longer time period (e.g., 75 seconds). It is within the scope and spirit of the present invention the the HIGH, MEDIUM, and LOW settings will drive the high voltage generator 170 for longer or shorter periods of time.

The MCU 130 provides the low voltage pulse signal, including "high" airflow signals and "low" airflow signals, to the high voltage generator 170, as described above. By way of example, the "high" airflow signal causes the voltage doubler 118 to provide 9KV to the first array 230, while 18KV is provided to the second array 240; and the "low" airflow signal causes the voltage doubler 118 to provide 6KV to the first array 230, while 12KV is provided to the second array 240. The voltage difference between the first array 230 and the second array 240 is proportional to the actual airflow output rate of the device 200. In general, a greater voltage differential is created between the first and second array by the "high" airflow signal. It is within the scope of the present invention for the MCU 130 and the high voltage generator 170 to produce other voltage potential differentials between the first and second arrays 230 and 240. The various circuits and components comprising the high voltage pulse generator 170 can, for example, be fabricated on a printed circuit board mounted within housing 210. The MCU 130 can be located on the same or a different circuit board.

As mentioned above, device 200 includes a boost button 216. In accordance with an embodiment of the present invention, when the MCU 130 detects that the boost button 216 has been depressed, the MCU 130 drives the high voltage generator 170 as if the control dial 214 was set to the HIGH setting for a predetermined amount of time (e.g., 5 minutes), even if the control dial 214 is set to LOW or MEDIUM (in effect overriding the setting specified by the dial 214). This will cause the device 200 will run at a maximum airflow rate for the boost time period (e.g., a 5 minute period). Alternatively, the MCU 130 can drive the high voltage generator 170 to even further increase the ozone and particle capture rate for the boost time period. For example, the MCU 130 can continually provide the "high" airflow signal to the high voltage generator 170 for the entire boost time period, thereby creating increased amounts of ozone. The increased amounts of ozone will reduce the odor in a room faster than if the device 200 was set to HIGH. The maximum airflow rate will also increase the particle capture rate of the device 200. In a preferred embodiment, pressing the boost button 216 will increase the airflow rate and ozone production continuously for 5 minutes. This time period may be longer or shorter. At the end of the preset time period (e.g., 5 minutes), the device 200 will return to the airflow rate previously selected by the control dial 214.

The MCU 130 can provide various timing and maintenance features. For example, the MCU 130 can provide a cleaning reminder feature (e.g., a 2 week timing feature) that provides a reminder to clean the device 200 (e.g., by causing indicator light 219 to turn on amber, and/or by triggering an audible alarm (not shown) that produces a buzzing or beeping noise). The MCU 130 can also provide arc sensing, suppression and indicator features, as well as the ability to shut down the high voltage generator 170 in the case of continued arcing. These and other features are described in additional detail below.

Arc Sensing and Suppression:

FIG. 8

Figure 8:
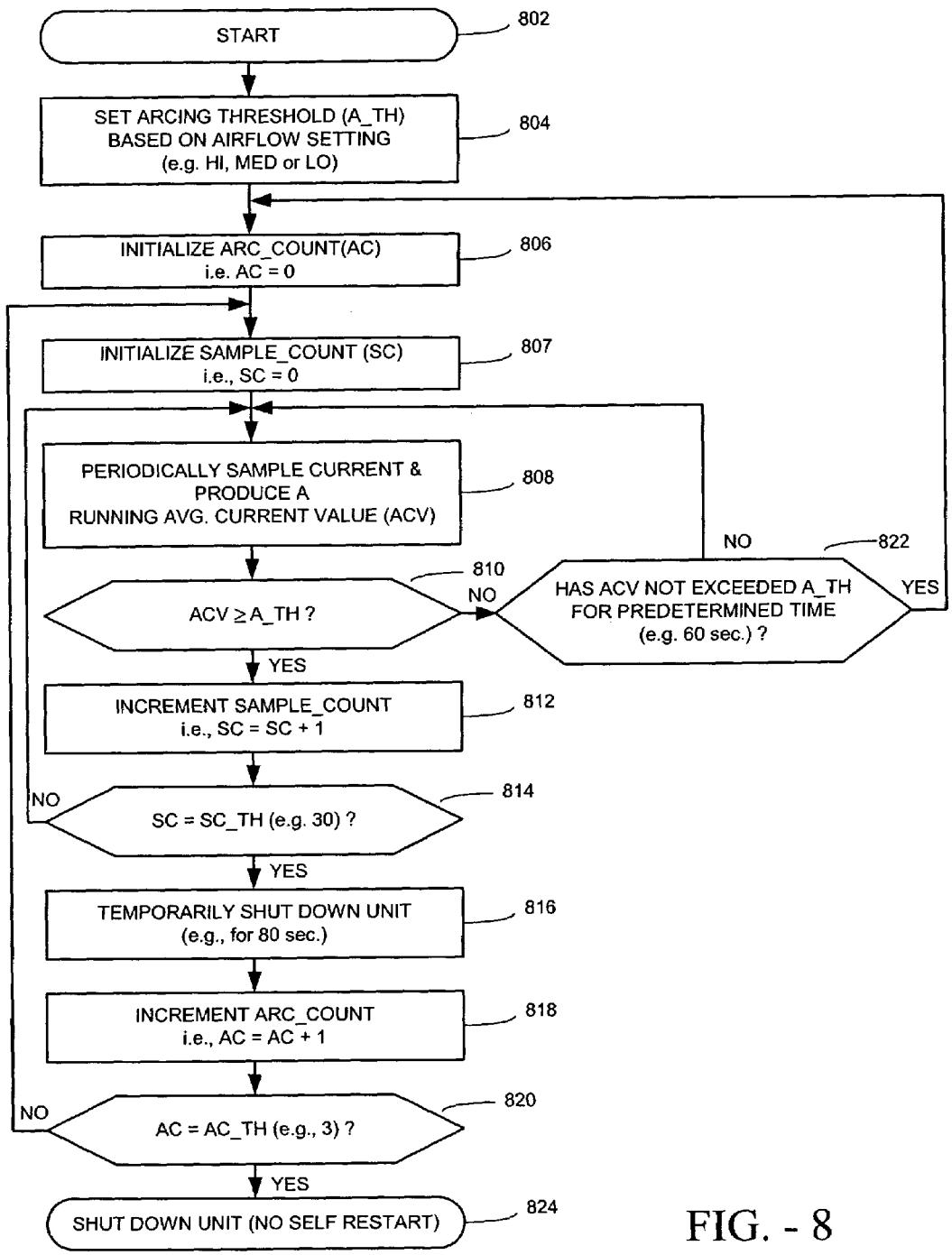
FIG. 8 is a flow diagram used to describe embodiments of the present invention that sense and suppress arcing.

The flow diagram of FIG. 8 is used to describe embodiments of the present invention that sense and suppress arcing between the first electrode array 230 and the second electrode array 240. The process begins at step 802, which can be when the function dial is turned from "OFF" to "ON" or "GP/ON." At a step 804, an arcing threshold is set, based on the airflow setting specified (by a user) using the control dial 214. For example, there can be a high threshold, a medium threshold and a low threshold. In accordance with an embodiment of the present invention, these thresholds are current thresholds, but it is possible that other thresholds, such as voltage thresholds, can be used. At a step 806, an arc count is initialized. At a step 807 a sample count is initialized.

At a step 808, a current associated with the electro-kinetic system is periodically sampled (e.g., one every 10 msec) to produce a running average current value. In accordance with an embodiment of the present invention, the MCU 130 performs this step by sampling the current at the emitter of the IGBT 126 of the high voltage generator 170 (see FIG. 7). The running average current value can be determined by averaging a sampled value with a previous number of samples (e.g., with the previous three samples). A benefit of using averages, rather than individual values, is that averaging has the effect of filtering out and thereby reducing false arcing detections. However, in alternative embodiments no averaging is used.

At a next step 810, the average current value determined at step 808 is compared to the threshold value, which was specified at step 804. If the average current value does not equal or exceed the threshold value (i.e., if the answer to step 810 is NO), then there is a determination at step 822 of whether the threshold has not been exceeded during a predetermined amount of time (e.g., over the past 60 seconds). If the answer to step 822 is NO (i.e., if the threshold has been exceeded during the past 60 seconds), then flow returns to step 808, as shown. If the answer to step 822 is YES, then there is an assumption that the cause for any previous arcing is no longer present, and flow returns to step 806 and the arc count and the sample count are both reinitialized. Returning to step 810, if the average current value reaches the threshold, then it is assumed that arcing has been detected (because arcing will cause an increase in the current), and the sample count is incremented at a step 812.

The sample count is then compared to a sample count threshold (e.g., the sample count threshold=30) at a step 814. Assuming, for example, a sample count threshold of 30, and a sample frequency of 10 msec, then the sample count equaling the sample count threshold corresponds to an accumulated arcing time of 300 msec (i.e., 10 msec*30=300 msec). If the sample count has not reached the sample count threshold (i.e., if the answer to step 814 is NO), then flow returns to step 808. If the sample count equals the sample count threshold, then the MCU 130 temporarily shuts down the high voltage generator 170 (e.g., by not driving the generator 170) for a predetermined amount of time (e.g., 80 seconds) at a step 816, to allow a temporary condition causing the arcing to potentially go away. For examples: temporary humidity may have caused the arcing; or an insect temporarily caught between the electrode arrays 230 and 240 may have caused the arcing. Additionally, the arc count is incremented at step 818.

At a step 820, there is a determination of whether the arc count has reached the arc count threshold (e.g., the arc count threshold=3), which would indicate unacceptable continued arcing. Assuming, for example, a sample count threshold of 30, and a sample frequency of 10 msec, and an arc count threshold of 3, then the arc count equaling the arc count threshold corresponds to an accumulated arcing time of 900 msec (i.e., 3*10 msec*30=300 msec). If the arc count has not reached the arc count threshold (i.e., if the answer to step 820 is NO), then flow returns to step 807, where the sample count is reset to zero, as shown. If the arc count equals the arc count threshold (i.e., if the answer to step 820 is YES), then the high voltage generator 170 is shut down at step 824, to prevent continued arcing from damaging to the device 200 or producing excessive ozone. At this point, the MCU 130 causes the overload/cleaning light 219 to light up red, thereby notifying the user that the device 200 has been "shut down." The term "shut down," in this respect, means that the MCU 130 stops driving the high voltage generator 170, and thus the device 200 stops producing ion and ozone containing airflow. However, even after "shut down," the MCU 130 continues to operate.

Once the device 200 is shut down at step 824, the MCU 130 will not again drive the high voltage generator 170 until the device 200 is reset. In accordance with an embodiment of the present invention, the device 200 can be reset by turning it off and back on (e.g., by turning function dial 218 to "OFF" and then to "ON" or "ON/GP"), which will in effect re-initialize the counters at step 806 and 807. Alternatively, or additionally, the device 200 includes a sensor, switch, or other similar device, that is triggered by the removal of the second electrode array 240 (presumably for cleaning) and/or by the replacement of the second electrode array 240. The device can alternately or additionally include a reset button or switch. The sensor, switch, reset button/switch or other similar device, provides a signal to the MCU 130 regarding the removal and/or replacement of the second electrode array 240, causing the MCU 130 to re-initialize the counters (at step 806 and 807) and again drive the high voltage generator 170.

Arcing can occur, for example, because of a carbon path is produced between the first electrode array 230 and the second electrode array 240, e.g., due to a moth or other insect that got caught in the device 200. Assuming the first and/or second electrode arrays 230 and 240 are appropriately cleaned prior to the device 200 being reset, the device should operate normally after being reset. However, if the arc causing condition (e.g., the carbon path) persists after the device 200 is reset, then the features described with reference to FIG. 8 will quickly detect the arcing and again shut down the device 200.

More generally, embodiments of the present invention provide for temporary shut down of the high voltage generator 170 to allow for a temporary arc creating condition to potentially go away, and for a continued shut down of the high voltage generator 170 if the arcing continues for an unacceptable duration. This enables the device 200 to continue to provide desirable quantities of ions and ozone (as well as airflow) following temporary arc creating conditions. This also provides for a safety shut down in the case of continued arcing.

In accordance with alternative embodiments of the present invention, at step 816 rather than temporarily shutting down the high voltage generator 170 for a predetermined amount of time, the power is temporarily lowered. The MCU 130 can accomplish this by appropriately adjusting the signal that it uses to drive the high voltage generator 170. For example, the MCU 130 can reduce the pulse width, duty cycle and/or frequency of the low voltage pulse signal provided to switch 126 for a predetermined amount of time before returning the low voltage pulse signal to the level specified according to the setting of the control dial 214. This has the effect of reducing the potential difference between the arrays 230 and 240 for the predetermined amount of time.

It would be apparent to one of ordinary skill in the relevant art that some of the steps in the flow diagram of FIG. 8 need not be performed in the exact order shown. For example, the order of steps 818 and 816 can be reversed or these steps can be performed simultaneously. However, it would also be apparent to one of ordinary skill in the relevant art that some of the steps should be performed before others. This is because certain steps use the results of other steps. The point is, the order of the steps is typically only important where a step uses results of another step. Accordingly, one of ordinary skill in the relevant art would appreciate that embodiments of the present invention should not be limited to the exact orders shown in the figures. Additionally, one of ordinary skill in the relevant art would appreciate that embodiments of the present invention can be implemented using subgroups of the steps that are shown in the figures.

In accordance with embodiments of the present invention, rather than periodically sampling a current or voltage associated with the electro-kinetic system at step 808, the MCU 130 can more continually monitor or sample the current or voltage associated with the electro-kinetic system so that even narrow transient spikes (e.g., of about 1 msec. in duration) resulting from arcing can be detected. In such embodiments, the MCU 130 can continually compare an arc sensing signal to an arcing threshold (similar to step 810). For example, when the arc sensing signal reaches or exceeds the arcing threshold a triggering event occurs that causes the MCU 130 to react (e.g., by incrementing a count, as in step 812). If the arcing threshold is exceeded more than a predetermined number of times (e.g., once, twice or three times, etc.) within a predetermined amount of time, then the unit 200 is temporarily shut down (similar to steps 810–816). If arcing is not detected for a predetermined amount of time, then an arcing count can be reset (similar to step 822). Thus, the flow chart of FIG. 8 applies to these event type (e.g., by interrupt) monitoring embodiments.

Other Electrode Configurations:

In practice, unit 200 is placed in a room and connected to an appropriate source of operating potential, typically 110 VAC. The energizing ionization unit 200, emits ionized air and ozone via outlet vents 260. The airflow, coupled with the ions and ozone freshens the air in the room, and the ozone can beneficially destroy or at least diminish the undesired effects of certain odors, bacteria, germs, and the like. The airflow is indeed electro-kinetically produced, in that there are no intentionally moving parts within unit. (Some mechanical vibration may occur within the electrodes).

In the various embodiments, electrode assembly 220 comprises a first array 230 of at least one electrode or conductive surface, and further comprises a second array 240 of at least one electrode or conductive surface. Material(s) for electrodes, in one embodiment, conduct electricity, are resistant to corrosive effects from the application of high voltage, yet be strong enough to be cleaned.

In the various electrode assemblies to be described herein, electrode(s) 232 in the first electrode array 230 can be fabricated, for example, from tungsten. Tungsten is sufficiently robust in order to withstand cleaning, has a high melting point to retard breakdown due to ionization, and has a rough exterior surface that seems to promote efficient ionization. On the other hand, electrode(s) 242 in the second electrode array 240 can have a highly polished exterior surface to minimize unwanted point-to-point radiation. As such, electrode(s) 242 can be fabricated, for example, from stainless steel and/or brass, among other materials. The polished surface of electrode(s) 242 also promotes ease of electrode cleaning.

The electrodes can be lightweight, easy to fabricate, and lend themselves to mass production. Further, electrodes described herein promote more efficient generation of ionized air, and appropriate amounts of ozone, (indicated in several of the figures as $O_3$).

Various electrode configurations for use in the device 200 are described in U.S. patent application Ser. No. 10/074,082, filed Feb. 12, 2002, entitled "Electro-Kinetic Air Transporter-Conditioner Devices with an Upstream Focus Electrode," incorporated herein by reference, and in the related application mentioned above.

In one embodiment, the positive output terminal of high voltage generator 170 is coupled to first electrode array 230, and the negative output terminal is coupled to second electrode array 240. It is believed that with this arrangement the net polarity of the emitted ions is positive, e.g., more positive ions than negative ions are emitted. This coupling polarity has been found to work well, including minimizing unwanted audible electrode vibration or hum. However, while generation of positive ions is conducive to a relatively silent airflow, from a health standpoint, it is desired that the output airflow be richer in negative ions, not positive ions. It is noted that in some embodiments, one port (such as the negative port) of the high voltage pulse generator 170 can in fact be the ambient air. Thus, electrodes in the second array need not be connected to the high voltage pulse generator using a wire. Nonetheless, there will be an "effective connection" between the second array electrodes and one output port of the high voltage pulse generator, in this instance, via ambient air. Alternatively the negative output terminal of the high voltage pulse generator 170 can be connected to the first electrode array 230 and the positive output terminal can be connected to the second electrode array 240. In either embodiment, the high voltage generator 170 will produce a potential difference between the first electrode array 230 and the second electrode array 240.

When voltage or pulses from high voltage pulse generator 170 are coupled across first and second electrode arrays 230 and 240, a plasma-like field is created surrounding electrodes in first array 230. This electric field ionizes the ambient air between the first and second electrode arrays and establishes an "OUT" airflow that moves towards the second array.

Ozone and ions are generated simultaneously by the first array electrodes 230, essentially as a function of the potential from generator 170 coupled to the first array of electrodes or conductive surfaces. Ozone generation can be increased or decreased by increasing or decreasing the potential at the first array. Coupling an opposite polarity potential to the second array electrodes 240 essentially accelerates the motion of ions generated at the first array, producing the out airflow. As the ions and ionized particulate move toward the second array, the ions and ionized particles push or move air molecules toward the second array. The relative velocity of this motion may be increased, by way of example, by decreasing the potential at the second array relative to the potential at the first array.

For example, if +10 KV were applied to the first array electrode(s), and no potential were applied to the second array electrode(s), a cloud of ions (whose net charge is positive) would form adjacent the first electrode array. Further, the relatively high 10 KV potential would generate substantial ozone. By coupling a relatively negative potential to the second array electrode(s), the velocity of the air mass moved by the net emitted ions increases.

On the other hand, if it were desired to maintain the same effective outflow (OUT) velocity, but to generate less ozone, the exemplary 10 KV potential could be divided between the electrode arrays. For example, generator 170 could provide +4 KV (or some other fraction) to the first array electrodes and −6 KV (or some other fraction) to the second array electrodes. In this example, it is understood that the +4 KV and the −6 KV are measured relative to ground. Understandably it is desired that the unit 200 operates to output appropriate amounts of ozone. Accordingly, in one embodiment, the high voltage is fractionalized with about +4 KV applied to the first array electrodes and about −6 KV applied to the second array electrodes.

In one embodiment, electrode assembly 220 comprises a first array 230 of wire-shaped electrodes, and a second array 240 of generally "U"-shaped electrodes 242. In some embodiments, the number N1 of electrodes comprising the first array 230 can differ by one relative to the number N2 of electrodes comprising the second array 240. In many of the embodiments shown, N2>N1. However, if desired, additional first electrodes could be added at the outer ends of array such that N1>N2, e.g., five first electrodes compared to four second electrodes.

As previously indicated first or emitter electrodes 232 can be lengths of tungsten wire, whereas collector electrodes 242 can be formed from sheet metal, such as stainless steel, although brass or other sheet metal could be used. The sheet metal can be readily configured to define side regions and bulbous nose region, forming a hollow, elongated "U"-shaped electrodes, for example.

In one embodiment, the spaced-apart configuration between the first and second arrays 230 and 240 is staggered. Each first array electrode 232 can be substantially equidistant from two second array electrodes 242. This symmetrical staggering has been found to be an efficient electrode placement. The staggering geometry can be symmetrical in that adjacent electrodes or adjacent electrodes are spaced-apart a constant distance, Y1 and Y2 respectively. However, a non-symmetrical configuration could also be used. Also, it is understood that the number of electrodes may differ from what is shown.

In one embodiment ionization occurs as a function of a high voltage electrodes. For example for increasing the peak to peak voltage amplitude and the duty cycle of the pulses form the high voltage pulse generator 170 can increase ozone content in the output flow of ionized air.

In one embodiment, the second electrodes 242 can include a trail electrode pointed region which help produce the output of negative ions. In one embodiment the electrodes of the second array 242 of electrodes is "U" shaped. One embodiment a single pair of "L" shaped electrode(s) in cross section can be additionally used.

In one embodiment, the electrodes assembly 220 has a focus electrode(s). The focus electrodes can produce an enhanced air flow exiting the devices. The focus electrode can have a shape that does not have sharp edges manufactured from a material that will not erode or oxides existing with steel. In one embodiment, the diameter of the focus electrode is 15 times greater than the diameter of the first electrode. The diameter of the focus electrode can be selected such that the focus electrode does not function as an ion generating surface. In one embodiment, the focus electrodes are electrically connected to the first array 230. Focus electrodes help direct the air flow toward the second electrode for guiding it towards particles towards the trailing sides of the second electrode.

The focus electrodes can be "U" or "C" shaped with holes extending there through to minimize the resistance of the focus electrode on the air flow rate. In one embodiment, the electrode assembly 220 has a pin-ring electrode assembly. The pin-ring electrode assembly includes a pin, cone or triangle shaped, first electrode and a ring shaped second electrode (with an opening) down-stream of the first electrode.

The system can use an additional downstream trailing electrode. The trailing electrode can be aerodynamically smooth so as not to interfere with the air flow. The trailing electrodes can have a negative electoral charge to reduce positive charged particles in the air flow. Trailing electrodes can also be floating or set to ground. Trailing electrodes can act as a second surface to collect positively charged particles. Trailing electrodes can also reflect charged particles towards the second electrodes 242. The trailing electrodes can also emit a small amount of negative ions into the air flow which can neutralize the positive ions emitted by the first electrodes 232.

The assembly can also use interstitial electrodes positioned between the second electrodes 242. The interstitial electrodes can float, be set to ground, or be put at a positive high voltage, such as a portion of the first electrode voltage. The interstitial electrodes can deflect particulate towards the second electrodes.

The first electrodes 232 can be made slack, kinked or coiled in order to increase the amount of ions emitted by the first electrode array 230. Additional details about all of the above described electrode configurations are provided in the above mentioned applications, that have been incorporated herein by reference.

The foregoing description of the preferred embodiments of the present invention has been provided for the purposes of illustration and description. It is not intended to be exhaustive or to limit the invention to the precise forms disclosed. Many modifications and variations will be apparent to the practitioner skilled in the art. Modifications and variations may be made to the disclosed embodiments without departing from the subject and spirit of the invention as defined by the following claims. Embodiments were chosen and described in order to best describe the principles of the invention and its practical application, thereby enabling others skilled in the art to understand the invention, the various embodiments and with various modifications that are suited to the particular use contemplated. It is intended that the scope of the invention be defined by the following claims and their equivalents.

What is claimed is:

1. A method for monitoring and suppressing arcing between a first electrode and a second electrode of an electro-kinetic system, the method including:
    (a) monitoring a current associated with the electro-kinetic system in order to adjust a first count and a second count;
    (b) each time a monitored current value reaches a current threshold, incrementing the first count;
    (c) each time the first count reaches a first count threshold, temporarily shutting down the electro-kinetic system for a predetermined period, incrementing the second count, and re-initializing the first count, wherein the electro-kinetic system restarts after the predetermined period; and (d) when the second count reaches a second count threshold, shutting down the electrokinetic system until a reset condition is satisfied.

2. The method of claim 1, wherein:
step (a) includes periodically sampling the current associated with the electro-kinetic system; and
step (b) includes comparing the samples produce at step (a) to the current threshold.

3. The method of claim 1, wherein:
step (a) includes periodically sampling the current associated with the electro-kinetic system and determining a running average of the samples; and step (b) includes comparing the running averages produced at step (a) to the current threshold.

4. The method of claim 3, wherein step (a) includes producing the running averages by averaging a most recent sample with a plurality of immediately proceeding samples.

5. The method of claim 1, wherein the electro-kinetic system remains off, after the second count reaches the second count threshold, until the second electrode is removed and replaced, thereby satisfying the reset condition.

6. The method of claim 1, wherein the electro-kinetic system remains off, after the second count reaches the second count threshold, until a power control switch is turned off and back on, thereby satisfying the reset condition.

7. The method of claim 1, further comprising:
after the second count reaches the second count threshold, resetting the first and second counts and restarting the electro-kinetic system in response to detecting removal and replacement of the second electrode.

8. The method of claim 1, further comprising:
re-initializing the first and second counts when the sampled current does not exceed the current threshold for a further predetermined period.

9. The method of claim 1, further comprising:
re-initializing the first and second counts when the sampled current does not exceed the current threshold for about 60 seconds.

10. The method of claim 1, further comprising:
re-initializing the first and second counts each time a predetermined number of monitored current values in a row do not exceed the current threshold.

11. A method for monitoring and suppressing arcing between a first electrode and a second electrode of an electro-kinetic system, the method including:
(a) monitoring a current associated with the electro-kinetic system in order to adjust a first count and a second count;
(b) each time a monitored current value reaches a current threshold, incrementing the first count;
(c) each time the first count reaches a first count threshold, temporarily shutting down the electro-kinetic system for a predetermined period, incrementing the second count, and re-initializing the first count, wherein the electro-kinetic system restarts after the predetermined period; and
(d) when the second count reaches a second count threshold, indicating to a user that the second electrode should be cleaned.

12. The method of claim 11, wherein step (d) includes illuminating an indicator light.

13. The method of claim 11, wherein step (d) includes triggering an audible alarm.

14. The method of claim 12, wherein step (d) further comprises shutting down the electro-kinetic system when the second count reaches the second count threshold.

15. The method of claim 11, further comprising:
(e) when the second count reaches the second count threshold, shutting down the electrokinetic system until removal and replacement of the second electrode is detected.

16. The method of claim 11, further comprising:
(e) when the second count reaches the second count threshold, shutting down the electrokinetic system until replacement of the second electrode is detected.

17. A method for monitoring and suppressing arcing between a first electrode and a second electrode of an electro-kinetic system, the method comprising:
(a) monitoring a voltage associated with the electro-kinetic system in order to adjust a first count and a second count;
(b) each time a monitored voltage value reaches a voltage threshold, incrementing the first count;
(c) each time the first count reaches a first count threshold, temporarily shutting down the electro-kinetic system for a predetermined period, incrementing the second count, and re-initializing the first count, wherein the electro-kinetic system restarts after the predetermined period; and
(d) when the second count reaches a second count threshold, shutting down the electrokinetic system until a reset condition is satisfied.

18. The method of claim 17, wherein:
step (a) includes periodically sampling the voltage associated with the electro-kinetic system; and
step (b) includes comparing the samples produce at step (a) to the voltage threshold.

19. The method of claim 17, wherein:
step (a) includes periodically sampling the voltage associated with the electro-kinetic system and determining a running average of the samples; and
step (b) includes comparing the running averages produced at step (a) to the voltage threshold.

20. The method of claim 19, wherein step (a) includes producing the running averages by averaging a most recent sample with a plurality of immediately proceeding samples.

21. The method of claim 17 wherein the electro-kinetic system remains off, after the second count reaches the second count threshold, until the second electrode is removed and replaced, thereby satisfying the reset condition.

22. The method of claim 17, wherein the electro-kinetic system remains off, after the second count reaches the second count threshold, until a power control switch is turned off and back on, thereby satisfying the reset condition.

23. A method for monitoring and suppressing arcing between a first electrode and a second electrode of an electro-kinetic system, the method including:
temporarily shutting down the electro-kinetic system when an accumulated arcing time reaches a first threshold;
shutting down the electro-kinetic system when the accumulated arcing time reaches a second threshold; and
after shut down due to the accumulated arcing time reaching the second threshold, restarting the electro-kinetic system in response to detecting removal and replacement of the second electrode.

24. A method for monitoring and suppressing arcing between a first electrode and a second electrode of an electro-kinetic system, the method including:
temporarily shutting down the electro-kinetic system when an accumulated arcing time reaches a first threshold;

shutting down the electro-kinetic system when the accumulated arcing time reaches a second threshold; and after shut down due to the accumulated arcing time reaching the second threshold, restarting the electro-kinetic system in response to detecting replacement of the second electrode.

25. A method for monitoring and suppressing arcing between a first electrode and a second electrode of an electrokinetic system, the method including:

temporarily shutting down the electro-kinetic system when an accumulated arcing time reaches a first thresholds shutting down the electro-kinetic system when the accumulated arcing time reaches a second threshold; and after shut down due to the accumulated arcing time reaching the second threshold, restarting the electro-kinetic system in response to detecting reset by a user.

26. A method for monitoring and suppressing arcing between a first electrode and a second electrode of an electro-kinetic system, the method including:

(a) monitoring a current associated with the electro-kinetic system;

(b) each time a monitored current value reaches a current threshold, incrementing a first count, wherein the current threshold is set based on an airflow setting; and (c) when the first count reaches a first count threshold, temporarily shutting down the electro-kinetic system.

27. A method for monitoring and suppressing arcing between a first electrode and a second electrode of an electro-kinetic system, the method including:

(a) monitoring a current associated with the electro-kinetic system;

(b) each time a monitored current value reaches a current threshold, incrementing a first count; and (c) when the first count reaches a first count threshold, temporarily shutting down the electro-kinetic system;

(d) when the first count reaches the first count threshold, incrementing a second count, and re-initializing the first count, such that the electro-kinetic system restarts after a predetermined period; and (e) when the second count reaches a second count threshold, shutting down the electro-kinetic system and indicating to a user that the system is shut down.

28. A method for monitoring and suppressing arcing between a first electrode and a second electrode of an electro-kinetic system, the method including:

(a) monitoring a current associated with the electro-kinetic system in order to adjust a first count and a second count;

(b) each time a monitored current value reaches a current threshold, incrementing the first count;

(c) each time the first count reaches a first count threshold, temporarily lowering a potential difference between the first and second electrodes from a set level for a predetermined period, incrementing the second count, and re-initializing the first count, wherein the potential difference between the first and second electrodes is returned to the set level after the predetermined period; and (d) when the second count reaches a second count threshold, indicating to a user that the second electrode should be cleaned.

29. A method for monitoring and suppressing arcing between a first electrode and a second electrode of an electro-kinetic system, the method including:

(a) sampling a current associated with the electro-kinetic system once every about 10 microseconds and producing a running average of the current samples; and (b) comparing the running average to a current threshold and incrementing a first count each time the running average reaches a current threshold;

(c) each time the first count reaches 30, temporarily shutting down the electro-kinetic system for about 80 seconds, incrementing a second count, and re-initializing the first count to equal 0, wherein the electro-kinetic system restarts after the about 80 seconds; and (d) when the second count reaches 3, shutting down the electro-kinetic system until a reset condition is satisfied.

30. The method of claim 29, wherein the electro-kinetic system remains off, after the second count reaches 3, until the second electrode is removed and replaced, thereby satisfying the reset condition.

31. A system for monitoring and suppressing arcing between a first electrode and a second electrode of an electro-kinetic system, comprising:

means for monitoring an accumulated arcing time;

means for shutting down the electro-kinetic system when the accumulated arcing time reaches a first threshold; and means for shutting down the electro-kinetic system when the accumulated arcing time reaches a second threshold;

wherein, following the accumulated arcing time reaching the second threshold, the electro-kinetic system is not restarted until the second electrode has been removed and replaced.

32. An air-transporter conditioner device, comprising:

a housing defining an inlet and an outlet;

an electro-kinetic system including a first electrode, a second electrode, and a high voltage generator disposed in the housing, to create an airflow moving from the inlet to the outlet; and a micro-controller unit to control the electro-kinetic system;

wherein the micro-controller unit:

monitors an accumulated arcing time between the first electrode and the second electrode;

temporarily shuts down the electro-kinetic system when the accumulated arcing time reaches a first threshold; and shuts down the electro-kinetic system when the accumulated arcing time reaches a second threshold, such that following the accumulated arcing time reaching the second threshold, the electro-kinetic system is not restarted until the micro-controller receives an indication that the second electrode has been replaced.

33. An air-transporter conditioner device, comprising:

a housing defining an inlet and an outlet;

an electro-kinetic system including a first electrode, a second electrode and a high voltage generator, disposed in the housing, to create an airflow moving from the inlet to the outlet; and a micro-controller unit to control the electro-kinetic system;

wherein the micro-controller unit:

monitors a current associated with the electro-kinetic system in order to adjust a first count and a second count;

increments the first count, each time a monitored current value reaches a current threshold;

increments the second count, temporarily shuts down the electro-kinetic system for a predetermined period, and re-initializing the first count, each time the first count reaches a first count threshold; and shuts down the electro-kinetic system, when the second count reaches a second count threshold, until a reset condition is satisfied.

34. The device of claim 33, wherein the high voltage generator is coupled between the first electrode and the second electrode; and wherein the micro-controller unit drives the high voltage generator with a low voltage pulse signal.

35. The device of claim 34, wherein the micro-controller unit shuts down the electro-kinetic system by not providing the low voltage pulse signal to the high voltage generator.

36. The device of claim 33, wherein the micro-controller unit is adapted to detect whether the reset condition is satisfied.

37. The device of claim 36, wherein the reset condition comprises removal of the second electrode from the housing and return of the second electrode in the housing.

38. The device of claim 36, wherein the reset condition comprises return of the second electrode in the housing.

39. The device of claim 36, wherein the reset condition comprises the turning off and on of the device.

40. An air-transporter conditioner device, comprising:
a housing defining an inlet and an outlet;
an electro-kinetic system including a first electrode, a second electrode and a high voltage generator, disposed in the housing, to create an airflow moving from the inlet to the outlet; and a micro-controller unit to control the electro-kinetic system;

wherein the micro-controller unit:
monitors a current associated with the electro-kinetic system in order to adjust a first count and a second count;
increments the first count, each time a monitored current value reaches a current threshold;
increments the second count, temporarily lowers a potential difference between the first and second electrodes for a predetermined period, and re-initializing the first count, each time the first count reaches a first count threshold; and
shuts down the electro-kinetic system, when the second count reaches a second count threshold.

41. An air-transporter conditioner device, comprising:
a housing defining an inlet and an outlet;
an electro-kinetic system including a first electrode, a second electrode and a high voltage generator, disposed in the housing, to create an airflow moving from the inlet to the outlet; and a micro-controller unit to control the electro-kinetic system;
wherein the micro-controller unit:
monitors the electro-kinetic system in order to adjust a first count;
increments the first count, each time a monitored current or voltage value reaches a threshold;
resets the count, when the monitored current or voltage has not exceeded the threshold for a predetermined amount of time; and
shuts down the electro-kinetic system when the count reaches a count threshold.

* * * * *